(12) United States Patent
Nirogi et al.

(10) Patent No.: US 12,397,003 B2
(45) Date of Patent: Aug. 26, 2025

(54) AMORPHOUS PHARMACEUTICAL COMPOSITIONS OF ABIRATERONE ACETATE

(71) Applicant: SUVEN LIFE SCIENCES LIMITED, Hyderabad-Telangana (IN)

(72) Inventors: Ramakrishna Nirogi, Hyderabad-Telangana (IN); Dhanunjay Kumar Dogiparti, Hyderabad-Telangana (IN); Koteshwara Mudigonda, Hyderabad-Telangana (IN); Jyothsna Ravula, Hyderabad-Telangana (IN); Venkateswarlu Jasti, Hyderabad-Telangana (IN)

(73) Assignee: SUVEN LIFE SCIENCES LIMITED, Hyderabad-Telangana (IN)

( * ) Notice: Subject to any disclaimer, the term of this patent is extended or adjusted under 35 U.S.C. 154(b) by 737 days.

(21) Appl. No.: 17/775,863

(22) PCT Filed: Nov. 13, 2020

(86) PCT No.: PCT/IB2020/060691
§ 371 (c)(1),
(2) Date: May 10, 2022

(87) PCT Pub. No.: WO2021/094992
PCT Pub. Date: May 20, 2021

(65) Prior Publication Data
US 2022/0387451 A1 Dec. 8, 2022

(30) Foreign Application Priority Data

Nov. 14, 2019 (IN) .............. 201941046346

(51) Int. Cl.
*A61K 31/58* (2006.01)
*A61K 9/20* (2006.01)

(52) U.S. Cl.
CPC ............ *A61K 31/58* (2013.01); *A61K 9/2009* (2013.01); *A61K 9/2013* (2013.01); *A61K 9/2018* (2013.01); *A61K 9/2027* (2013.01); *A61K 9/2031* (2013.01); *A61K 9/2054* (2013.01)

(58) Field of Classification Search
CPC .... A61K 31/58; A61K 9/2009; A61K 9/2013; A61K 9/2018; A61K 9/2027; A61K 9/2031; A61K 9/2054
USPC ........................................... 514/176
See application file for complete search history.

(56) References Cited

U.S. PATENT DOCUMENTS

2019/0091339 A1 3/2019 Miller et al.

FOREIGN PATENT DOCUMENTS

WO 2013012959 A1 1/2013
WO 2014009437 A1 1/2014

OTHER PUBLICATIONS

Cancer [online], [retrieved on Jul. 6, 2007] Retrieved from the Internet, URL: http://www.nim.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Anonymous, Assessment Report for Zytiga (abiraterone), United Kingdom Committee for Medicinal Products for Human Use (CHMP), Jul. 21, 2011, EMA/CHMP/542871/2011, London, United Kingdom.
Gala et all, Harnessing the therapeutic potential of anticancer drugs through amorphous solid dispersions, BBA—Reviews on Cancer, 2020 188319, Austin, TX USA.
Solymosi et all, Novel formulation of abiraterone acetate might allow significant dose reduction and eliminates substantial positive food effect, Cancer Chemother Pharmacol, Aug. 3, 2017, Springer-Verlag GmbH, Germany 2017.
Applicant's Response to Written Opinion of International Preliminary Examining Authority dated Sep. 22, 2021; Response dated Nov. 20, 2021.
Applicant's Response to Written Opinion of the International Search Authority dated Mar. 15, 2021; Response dated May 14, 2021.
PCT, International Preliminary Report on Patentability dated Jan. 31, 2022.
PCT, International Search Report dated Mar. 15, 2021.
PCT, Written Opinion International Search Authority, 2021.
PCT, Written Opinion International Preliminary Examining Authority dated Sep. 22, 2021.

* cited by examiner

*Primary Examiner* — Kristin A Vajda
(74) *Attorney, Agent, or Firm* — IPHORGAN Ltd.

(57) ABSTRACT

The present invention relates to a pharmaceutical composition comprising solid dispersion of amorphous abiraterone acetate and one or more pharmaceutically acceptable excipients, having improved solubility, stability, bioavailability, and no positive food effect. The present invention also relates to a method for its preparation, a dosage form comprising such compositions, and the use of the said composition or dosage form as a medicament for the treatment of prostate cancer.

20 Claims, 3 Drawing Sheets

Figure-1: XRD of crystalline abiraterone acetate.
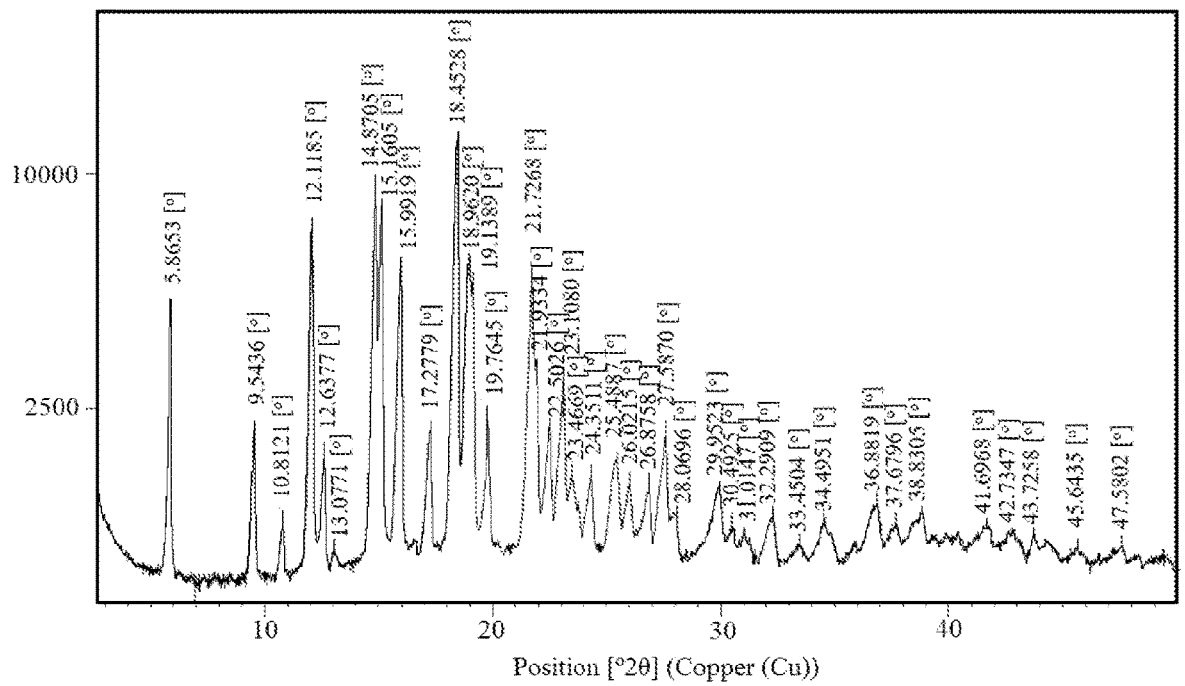
Figure-2: XRD of abiraterone acetate granules of Example 7.
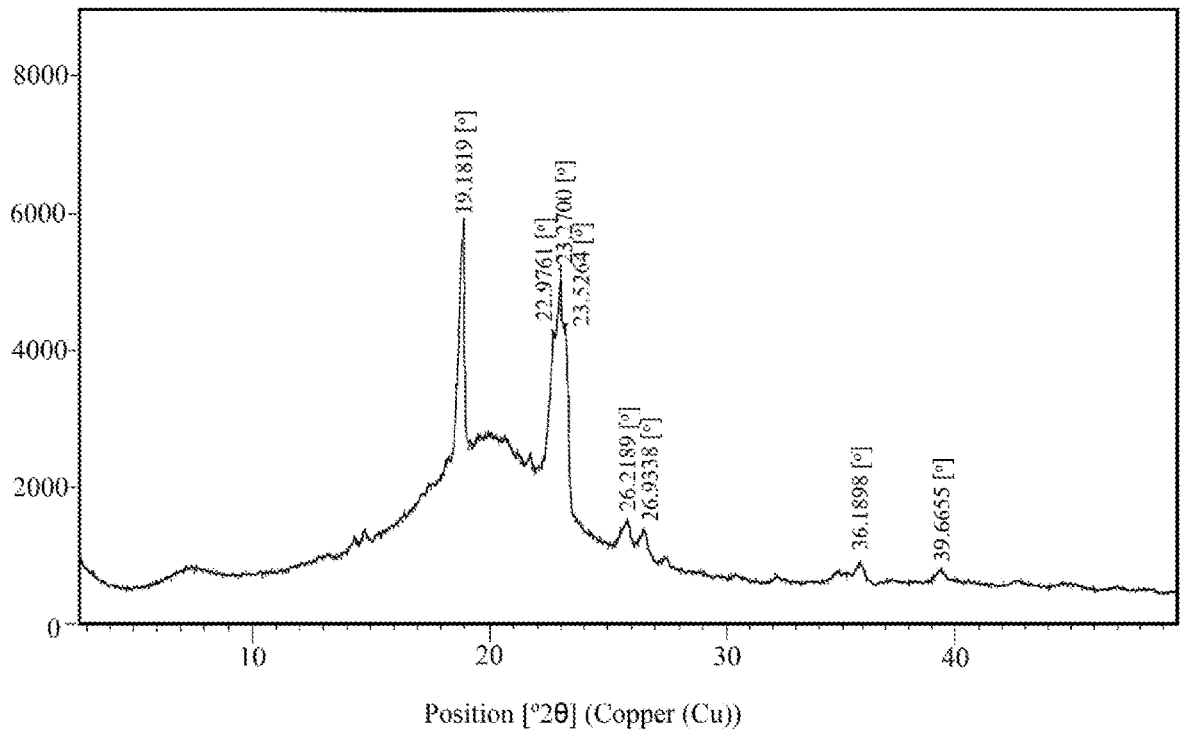

Figure-3: XRD of abiraterone acetate granules of Example 16, placebo and crystalline abiraterone acetate.
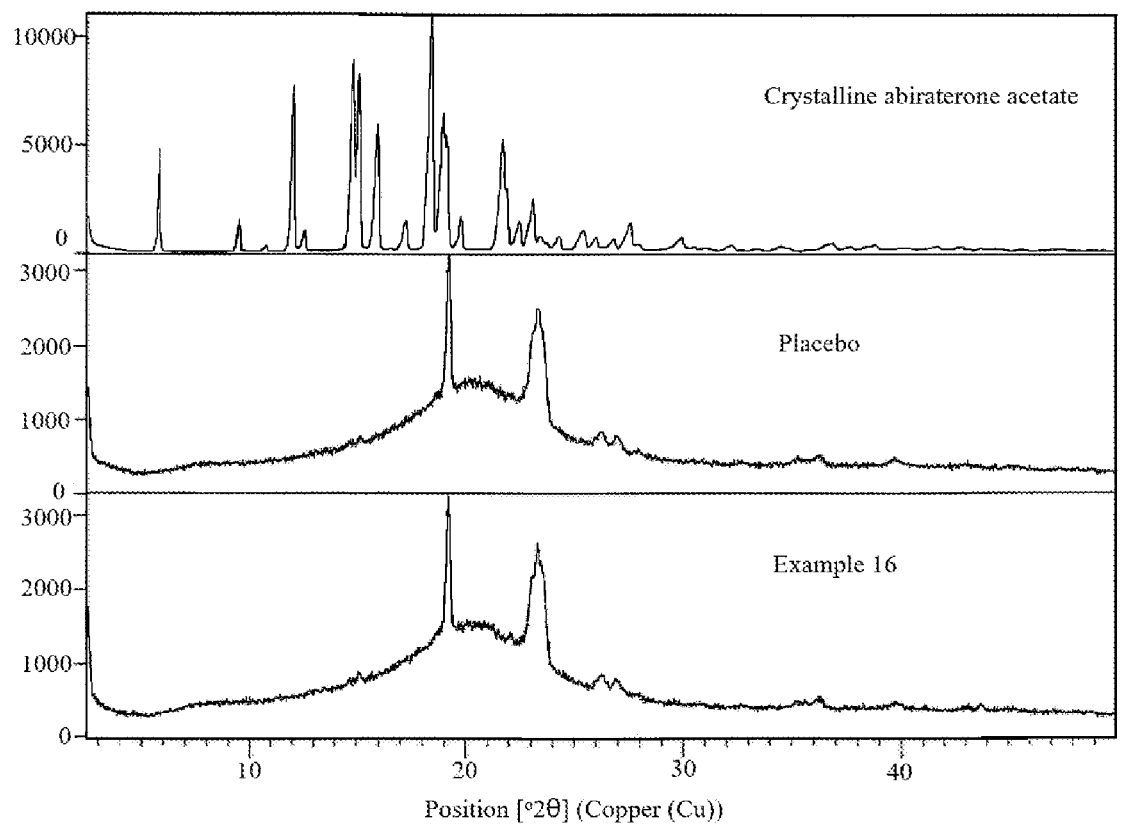
Figure-4: XRD of abiraterone acetate granules of Example 16 and placebo after six months.
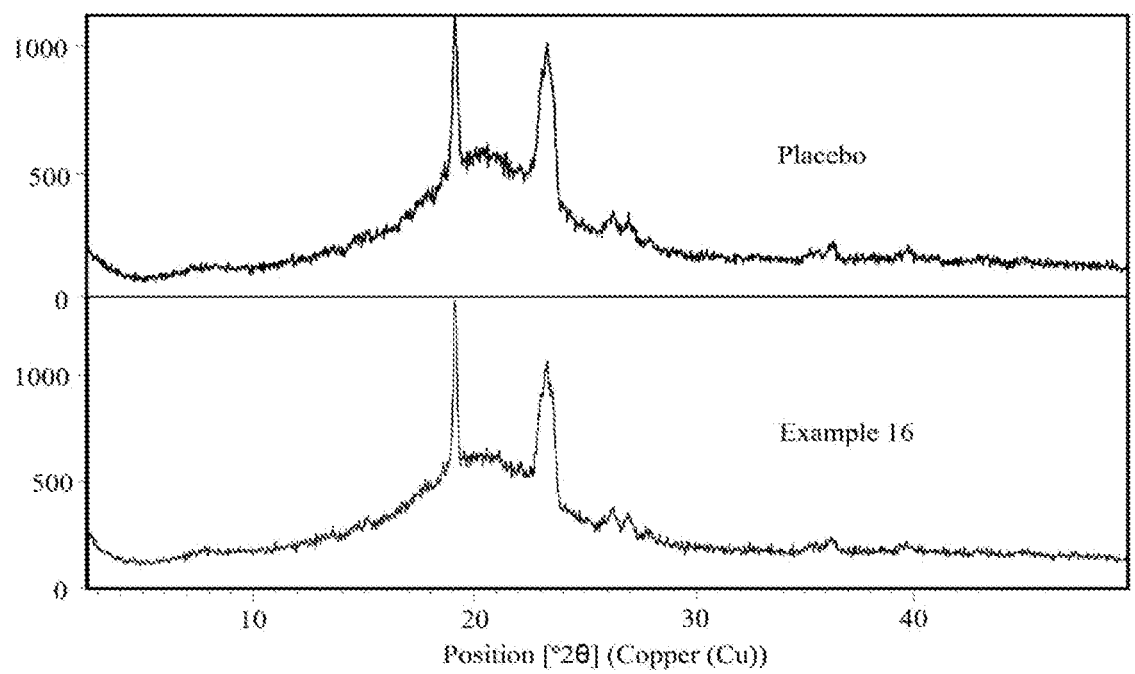

Figure-5: XRD of abiraterone acetate granules of Example 15 at initial day and after six months.
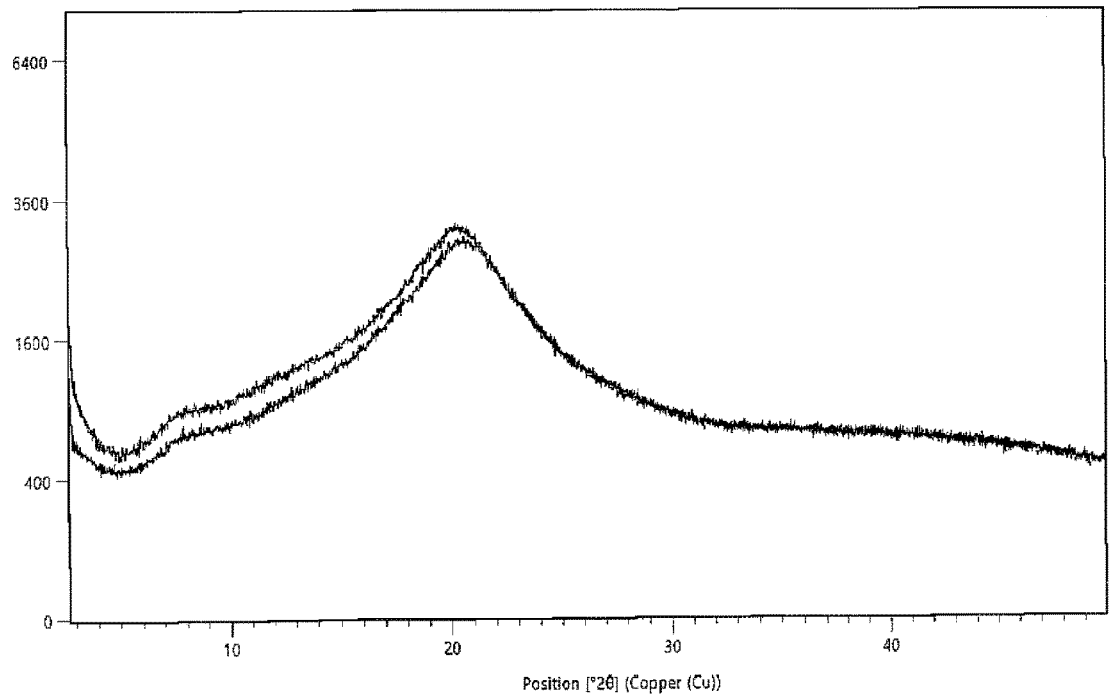
Figure-6: Particle size distribution of abiraterone acetate granules of Example 16.
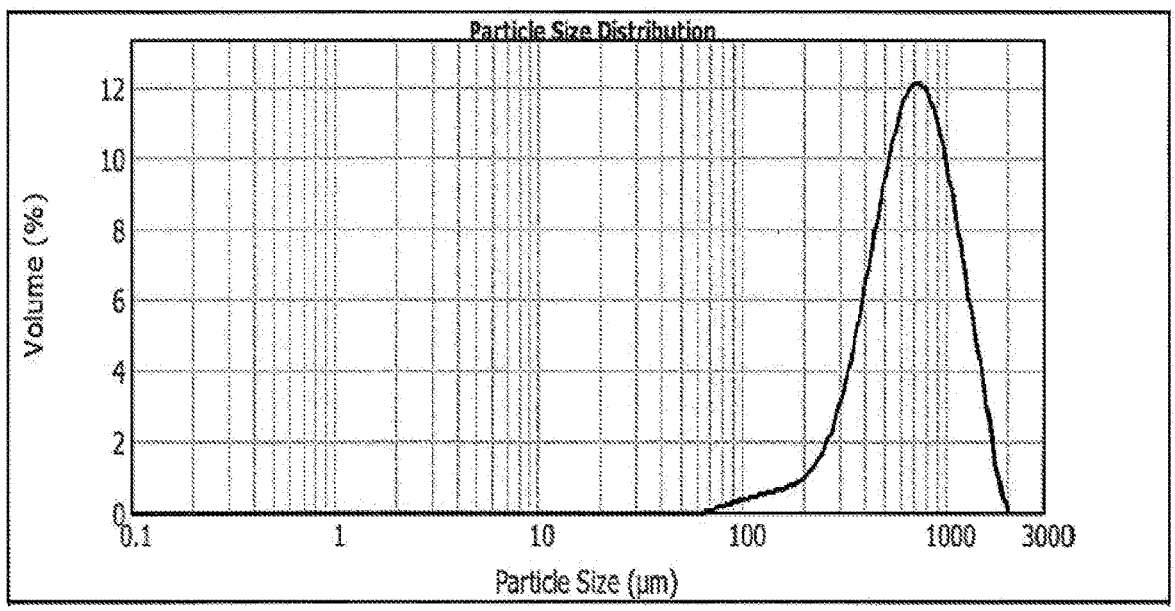

AMORPHOUS PHARMACEUTICAL COMPOSITIONS OF ABIRATERONE ACETATE

CROSS REFERENCE TO RELATED APPLICATIONS

This application is a national stage completion application of PCT Application No. PCT/IB2020/060691, filed Nov. 13, 2020, and claims priority from India application Ser. No. 20/194,1046346, filed Nov. 14, 2019. Each of these applications is incorporated by reference herein in its entirety.

FIELD OF THE INVENTION

The present invention relates to oral pharmaceutical compositions comprising solid dispersion of amorphous abiraterone acetate and one or more pharmaceutically acceptable excipients, methods of preparing and administering such pharmaceutical compositions.

BACKGROUND OF THE INVENTION

Prostate cancer is cancer that occurs in the prostate gland, a small walnut-shaped gland in men that produces the seminal fluid that nourishes and transports sperm. Prostate cancer is one of the most common types of cancer in men. Prostate cancer is the second most common cancer diagnosed in men living in the U.S.A.

Structure of Abiraterone Acetate:

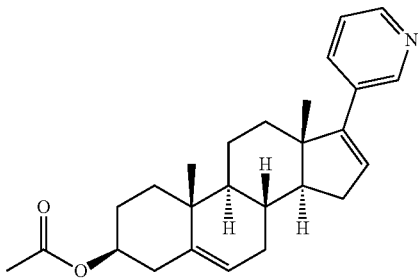

Abiraterone acetate is approved in the United States by USFDA as Zytiga® in April 2011, in combination with prednisone for the treatment of patients with metastatic castration-resistant prostate cancer (CRPC). The prescribing information for Zytiga® tablets recommends 1,000 mg (4×250 mg tablets) administered orally once daily in combination with prednisone (5 mg) administered orally twice daily. Abiraterone acetate is also approved in the United States by USFDA as YONSA® in May 2018 (500 mg administered orally once daily), in combination with methylprednisolone (4 mg) for the treatment of patients with CRPC.

Abiraterone acetate is a prodrug of abiraterone, which inhibits 17 α-hydroxylase/C17,20-lyase (CYP17) expressed in testicular, adrenal, and prostatic tumor tissues. Abiraterone acetate is highly lipophilic (Log P 5.12) and as a result suffers from low aqueous solubility in the gastrointestinal tract (Zytiga® Full Prescribing Information, 2012, Janssen Biotech Inc., Section 11).

Due to highly lipophilic nature and poor aqueous solubility in the gastrointestinal tract, the oral bioavailability of abiraterone acetate is limited. After an oral dose of abiraterone acetate, 88% of the administered drug gets excreted unchanged through feces, and another 5% is excreted in the urine (Ryan C J et al., *J ClinOncol.* 2010; 28(9):1481-1488). Therefore, >90% of the administered drug gets excreted and is not used for its intended treatment. Further Zytiga® tablets containing abiraterone acetate shows significant inter individual pharmacokinetic variability and positive food effect when administered with low-fat (7- and 5-fold increase in $C_{max}$ and $AUC_{0-\infty}$, respectively) or high-fat (17- and 10-fold increase in $C_{max}$ and $AUC_{0-\infty}$ respectively). As a result, Zytiga® must be taken on an empty stomach with water at least 2 hr before or 1 hr after a meal. There is a need for developing new pharmaceutical compositions for abiraterone acetate that improve bioavailability in the fasted state to in turn reduce the food effect and overall variability in absorption.

WO2016162229 had disclosed the capsule comprising the abiraterone acetate in a liquid or semi-solid lipid matrix (containing the surfactant and lipid). The liquid or semi-solid formulations comprising abiraterone possess stability and solubility issues.

To facilitate abiraterone acetate into pharmaceutical compositions, high solubility and stability of abiraterone acetate is desired. The solid dispersions of poorly soluble drugs in various types of excipients are known generally to improve the solubility of drug products. However, such dispersions are generally unstable over time. Amorphous dispersions of drugs in various types of excipients tend to convert to crystalline forms over time, which can lead to improper dosing due to differences in the bioavailability and solubility of crystalline drug material compared to amorphous drug material. One skilled in the art cannot predict what kind of techniques and excipients, would be useful for preparing stable amorphous solid dispersions for a particular drug product.

Thus, there is an unmet need to develop novel formulations comprising abiraterone acetate having improved solubility, stability, bioavailability, and no food effect. Such formulations of abiraterone acetate will have efficacy at much lower doses and also may result in reduction of food effect comparing marketed products.

Therefore, an objective of the present invention is to provide pharmaceutical compositions for abiraterone acetate having improved solubility, stability and bioavailability, and reduced food effect.

This objective is attained by developing a pharmaceutical composition comprising solid dispersion of amorphous abiraterone acetate and one or more pharmaceutically acceptable excipients. The compositions of the present invention comprising solid dispersion of amorphous abiraterone acetate possess improved solubility, stability, bioavailability, and no positive food effect compared to abiraterone acetate (Zytiga®).

SUMMARY OF THE INVENTION

In one aspect, the present invention relates to a pharmaceutical composition comprising solid dispersion of amorphous abiraterone acetate and one or more pharmaceutically acceptable excipients.

In another aspect, the present invention relates to a pharmaceutical composition comprising solid dispersion of amorphous abiraterone acetate, wherein said solid dispersion comprises based on the total weight of the composition:
(a) abiraterone acetate;
(b) one or more polymers;
(c) one or more surfactants;
(d) one or more plasticizers;

(e) a pH modifier;
(f) a disintegrating agent; and
(g) one or more preservatives.

In yet another aspect, the present invention relates to a pharmaceutical composition comprising solid dispersion of amorphous abiraterone acetate, wherein said solid dispersion comprises based on the total weight of the composition:
(a) from 2% to 50% by weight abiraterone acetate;
(b) from 10% to 75% by weight one or more polymers;
(c) from 10% to 70% by weight one or more surfactants;
(d) from 5% to 50% by weight one or more plasticizers;
(e) from 0.5% to 5% by weight at least one pH modifier;
(f) from 2% to 10% by weight at least one disintegrating agent; and
(g) from 0.01% to 1% by weight one or more preservatives.

In yet another aspect, the pharmaceutical compositions described in the present invention further comprise one or more pharmaceutically acceptable excipients selected from diluents, glidants, lubricants, sweetening agents, flavoring agents, coloring agents, effervescence agents, and a mixture of one or more thereof.

In yet another aspect, the present invention also relates to a method of preparation of the pharmaceutical compositions comprising solid dispersion of amorphous abiraterone acetate and optionally one or more pharmaceutically acceptable excipients.

In another aspect, the pharmaceutical compositions described in the present invention can be formulated as dosage forms include powders, pills, tablets, coated tablets, capsules, granules, pellets, patches, implants, films, liquids, semi-solids, gels, aerosols, emulsions, elixirs and the like.

In another aspect, the pharmaceutical compositions of the present invention comprising abiraterone acetate ranges from 5 mg to 500 mg, preferably ranges from 50 mg to 250 mg.

In another aspect, the total weight of the dosage form range from 0.1 gram to 10 grams.

In yet another aspect, the present invention relates to a method of preparing granules composition comprising the solid dispersion of amorphous abiraterone acetate and one or more pharmaceutical excipients as described above.

In yet another aspect, the present invention relates to a method of preparing the oral dosage compositions such as tablets, capsules, pills comprising the granules as mentioned above.

In yet another aspect, the present invention relates to the pharmaceutical composition comprising solid dispersion of amorphous abiraterone acetate for use in the treatment of cancers.

In yet another aspect, the present invention relates to the pharmaceutical compositions comprising solid dispersion of amorphous abiraterone acetate, for use in the treatment of cancers related to 17-α-hydroxylase/C17,20 lyase.

BRIEF DESCRIPTION OF DRAWINGS

FIG. 1: XRD of crystalline abiraterone acetate.
FIG. 2: XRD of abiraterone acetate granules of Example 7.
FIG. 3: XRD of abiraterone acetate granules of Example 16, placebo and crystalline abiraterone acetate.
FIG. 4: XRD of abiraterone acetate granules of Example 16 and placebo after six months.
FIG. 5: XRD of abiraterone acetate granules of Example 15 at initial day and after six months.
FIG. 6: Particle size distribution of abiraterone acetate granules of Example 16.

DETAILED DESCRIPTION OF THE INVENTION

Unless otherwise stated, the following terms used in the specification and claims have the meanings given below:

The term, "pharmaceutically acceptable excipients" as used herein refers to lipids, phospholipids, polymers, co-polymers, triglycerides, surfactants, film formers, disintegrating agent, plasticizers, pH modifiers, diluents, lubricants, glidants, coating agents, emulsifying agent, crystallization inhibitors/stabilizers, solvents (acetone, methanol, ethanol & isopropyl alcohol), preservatives, sweetening agents, flavouring agents, coloring agents, anti-oxidants, solubilizers, effervescent agent and the like.

The "polymer" employed in the composition of the present invention is capable of holding the ingredients together and forming the granules with the required mechanical strength.

The "surfactant" employed in the composition of the present invention is capable of solubilising the active ingredient.

The "plasticizer" employed in the composition of the present invention is capable of enhancing the plastic nature of the pharmaceutical dosage form.

The "diluent" employed in the composition of the present invention is capable of providing bulkiness to obtain a desired the pharmaceutical composition.

The "disintegrating agent" employed in the composition of the present invention is capable of facilitating the breakup of the pharmaceutical composition prepared from the composition when placed in contact with an aqueous medium.

The "lubricant" employed in the composition of the present invention is capable of preventing the ingredients from clumping together and from sticking to the apparatus on which it is formed, for example, preventing adherence to the face of the upper punch (picking) or lower punch (sticking) of the compression machine.

The "glidant" employed in the composition of the present invention is capable of increasing the flow.

The "pH modifier" employed in the composition of the present invention is capable to increase or decrease the acidity.

The "coloring agent" employed in the composition of the present invention may be one or more compounds that impart a desired color to the composition. The addition of a coloring agent may be used, for example, so that tablets of different potencies may be easily distinguished.

The term "solid dispersion" denotes a formulation wherein an active ingredient is dispersed in a molecular state or the form of fine particles in a hydrophilic carrier. The hydrophilic carrier majorly comprises polymers, surfactants, and plasticizers.

The term "active ingredient" (used interchangeably with "active" or "active substance" or "drug") used herein includes abiraterone or a pharmaceutically acceptable salt thereof. Preferably the active ingredient is abiraterone acetate.

The term "placebo" is that which cannot be differentiated from the active ingredient-containing compositions in color and/or texture without the presence of abiraterone acetate.

The terms "% by weight" or "wt %" or "% w/w" denote the weight of an individual component or a mixture of one or more components in the composition as a percentage of the weight of the composition.

The term "known impurity" as used herein refers to abiraterone and other minor impurities. Abiraterone is formed by conversion of abiraterone acetate in the dosage form. There are other minor impurities of abiraterone acetate which are significantly lower comparing to the known impurity of abiraterone. These minor impurities include 7-ketoabiraterone acetate, α-epoxyabiraterone acetate, β-epoxyabiraterone acetate, and abiraterone ethyl ether.

The term, "pharmaceutically acceptable salt" as used herein refers to salts of the active ingredient and are prepared by reaction with the appropriate acid or acid derivative, depending on the particular substituents found on the abiraterone. The salts are formed with inorganic acids e.g., hydrochloric, hydrobromic, sulfuric, nitric or phosphoric acid or organic acids e.g., oxalic, succinic, maleic, acetic, fumaric, citric, malic, tartaric, benzoic, p-toluic, p-toluenesulfonic, benzenesulfonic acid, methanesulfonic or naphthalenesulfonic acid.

The term "glucocorticoid" as used herein refers to a steroidal hormone such as prednisone, prednisolone, methylprednisolone, beclomethasone, betamethasone, budesonide, cortisone, dexamethasone, hydrocortisone, and triamcinolone.

The term, "patient" or "subject" as used herein refers to an animal. Preferably the term "patient" or "subject" as used herein refers to a mammal. The term mammal includes animals such as mice, rats, dogs, rabbits, pigs, monkeys, horses, and humans. More preferably the patient is human.

Embodiments

In one embodiment, the present invention relates to a pharmaceutical composition comprising solid dispersion of amorphous abiraterone acetate and one or more pharmaceutically acceptable excipients.

In some embodiments, the present invention relates to a pharmaceutical composition comprising solid dispersion comprising:
  (a) abiraterone acetate;
  (b) one or more polymer(s);
  (c) one or more surfactant(s);
  (d) one or more plasticizer(s);
  (e) a pH modifier;
  (f) at least one disintegrating agent; and
  (g) one or more preservative(s).

In some embodiments, the present invention relates to a pharmaceutical composition comprising solid dispersion comprising:
  (a) abiraterone acetate;
  (b) one or more polymer(s);
  (c) one or more surfactant(s);
  (d) one or more plasticizer(s);
  (e) a disintegrating agent; and
  (f) one or more preservative(s).

In some embodiments, the abiraterone acetate can be used in an amount range from 2% to 50% by weight, from 2% to 25% by weight, or from 3% to 15% by weight.

In some embodiments, the pharmaceutical composition of the present invention comprises abiraterone acetate in an amount range from 2% to 15% by weight.

In some embodiments, said one or more polymer(s) can be used in an amount of range from 15% to 30%, from 15% to 50%, or from 25% to 50% by weight, based on the total weight of the composition.

In some embodiments, said one or more surfactants can be used in an amount of range from 30% to 45%, from 30% to 60%, or from 30% to 70% by weight, based on the total weight of the composition.

In some embodiments, said one or more plasticizer(s) can be used in an amount range from 5% to 30%, or from 20% to 35% by weight, based on the total weight of the composition.

In some embodiments, the pH modifier can be used in an amount range from 0.2% to 5%, or from 1% to 5% by weight, based on the total weight of the composition.

In some embodiments, the disintegrating agent can be used in an amount range from 1% to 5%, or from 3% to 5% by weight, based on the total weight of the composition.

In some embodiments, said one or more preservative(s) can be used in an amount ranging from 0.01% to 0.1%, or from 0.01% to 0.5% by weight, based on the total weight of the composition.

In another embodiment, the present invention relates to a pharmaceutical composition comprising solid dispersion of amorphous abiraterone acetate, wherein said solid dispersion comprising based on the total weight of the composition:
  (a) from 2% to 25% by weight abiraterone acetate;
  (b) from 15% to 50% by weight one or more polymers;
  (c) from 30% to 70% by weight one or more surfactants;
  (d) from 5% to 35% by weight one or more plasticizers;
  (e) from 0.5% to 2% by weight at least one pH modifier;
  (f) from 2% to 10% by weight at least one disintegrating agent; and
  (g) from 0.01% to 0.5% by weight one or more preservatives.

In another embodiment, the present invention relates to a pharmaceutical composition comprising solid dispersion of amorphous abiraterone acetate, wherein said solid dispersion comprising based on the total weight of the composition:
  (a) from 3% to 5% by weight abiraterone acetate;
  (b) from 15% to 25% by weight one or more polymers;
  (c) from 30% to 45% by weight one or more surfactants;
  (d) from 20% to 30% by weight one or more plasticizers;
  (e) from 0.5% to 2% by weight at least one pH modifier;
  (f) from 3% to 5% by weight at least one disintegrating agent; and
  (g) from 0.01% to 0.2% by weight one or more preservatives.

In another embodiment, the present invention relates to a pharmaceutical composition comprising solid dispersion of amorphous abiraterone acetate, wherein said solid dispersion comprising based on the total weight of the composition:
  (a) from 3% to 5% by weight abiraterone acetate;
  (b) from 15% to 30% by weight one or more polymers;
  (c) from 30% to 60% by weight one or more surfactants;
  (d) from 5% to 30% by weight one or more plasticizers;
  (e) from 0.5% to 2% by weight at least one pH modifier;
  (f) from 3% to 5% by weight at least one disintegrating agent;
  (g) from 0.01% to 0.2% by weight one or more preservatives; and
  (h) from 0.5% to 2% by weight of at least one glidant.

In another embodiment, the present invention relates to a pharmaceutical composition comprising solid dispersion of amorphous abiraterone acetate, wherein said solid dispersion comprising based on the total weight of the composition:

(a) from 3% to 5% by weight abiraterone acetate;
(b) from 20% to 30% by weight one or more polymers;
(c) from 35% to 50% by weight one or more surfactants;
(d) from 20% to 30% by weight one or more plasticizers;
(e) from 0.5% to 2% by weight at least one pH modifier;
(f) from 3% to 5% by weight at least one disintegrating agent; and
(g) from 0.01% to 0.3% by weight at least one preservative.

In another embodiment, the present invention relates to a pharmaceutical composition comprising solid dispersion of amorphous abiraterone acetate, wherein said solid dispersion comprising based on the total weight of the composition:
(a) from 3% to 5% by weight abiraterone acetate;
(b) from 35% to 50% by weight one or more polymers;
(c) from 35% to 50% by weight one or more surfactants;
(d) from 5% to 30% by weight one or more plasticizers;
(e) from 0.5% to 2% by weight at least one pH modifier;
(f) from 3% to 5% by weight at least one disintegrating agent; and
(g) from 0.01% to 0.3% by weight at least one preservative.

The polymers used in the present invention include water-soluble polymers, pH-sensitive polymers, and a mixture of one or more thereof. The term "water-soluble polymers" as included in the present invention refers to polymers that are soluble in an aqueous medium with a pH range below 14. It may be ionic or neutral polymers with polar or charged functional groups.

Examples of water-soluble polymers suitable for use in the present invention include, but are not limited thereto, homopolymers and copolymers of N-vinyl lactams, especially homopolymers and copolymers of N-vinyl pyrrolidone, e.g. polyvinylpyrrolidone, copolymers of N-vinyl pyrrolidone and vinyl acetate, or vinyl propionate; lauroylpolyoxylglycerides, polyvinyl caprolactam-poly vinyl acetate-polyethylene glycol graft copolymer; cellulose esters and cellulose ethers, in particular methylcellulose; hydroxyalkylcelluloses, in particular hydroxypropylcellulose; hydroxyalkylalkylcelluloses, in particular hydroxypropylmethylcellulose; high molecular polyalkylene oxides such as polyethylene oxide, polypropylene oxide, copolymers of ethylene oxide and propylene oxide; poly(hydroxyalkyl acrylates), poly(hydroxyalkylmethacrylates), polyacrylate, polymethylacrylate, polyacrylamides, vinyl acetate polymers such as copolymers of vinyl acetate and crotonic acid, partially hydrolyzed polyvinyl acetate (also referred to as partially saponified "polyvinyl alcohol"), polysaccharides such as hyaluronic acid, dextran, carrageenans, galactomannans and xanthan gum, or mixtures of one or more thereof.

The pH-sensitive polymers can be used in the present invention include enteric polymers and gastric soluble polymers.

The term "enteric polymers" as included in the present invention have pH-dependent solubility in the gastrointestinal tract which has solubility resistance in gastric fluid (at or around pH 1-4) but will have solubility when the pH of the fluid increases such as in the intestinal tract (above pH 5).

Examples of enteric polymers suitable for use in the present invention include, but are not limited to, cellulose derivatives such as cellulose acetate phthalate (CAP), hydroxypropyl methylcellulose phthalate (HPMCP-50 or HPMCP-55), hydroxypropyl methylcellulose acetate succinate (HPMCAS), alkali-soluble acrylic copolymers (Eudragit® L series and Eudragit® S series), polyvinyl acetate phthalate (PVAP), alginates, carboxymethyl cellulose (CMC), or any combinations thereof.

The term "gastric-soluble polymers" as included in the present invention have pH-dependent solubility in the gastrointestinal tract which is soluble in gastric fluid (at or around pH 1-4) but will not have solubility when the pH of the fluid increases such as in the intestinal tract (above pH 5).

Examples of gastric-soluble polymers suitable for use in the present invention include, but are not limited to, methacrylic acid copolymers selected from Eudragit® E100 (also referred to as butylmethacrylatedimethylaminoethyl methacrylate-methylmethacrylate-copolymer (1:2:1), chitosan and its derivatives (linear polysaccharide composed of randomly distributed P-(1-4)-linked D-glucosamine (deacetylated unit) and N-acetyl-D-glucosamine (acetylated unit), which are made by treating shrimp and other crustacean shells with alkali sodium hydroxide), or other high molecular weight polymers with at least one cationic functional group, or any combinations thereof.

Other polymers suitable for use in the present invention include dextrin, pullulan, acacia, tragacanth, sodium alginate, propylene glycol alginate, agar powder, phospholipids (lecithin), glucomannan, processed starch (rice, potato, pea, pregelatinized), gelatin, pectin, low viscosity pectin, casein, whey protein extract, soy protein extract, zein, levan, elsinan, gluten, acacia gum, carrageenan, arabic gum, guar gum, locust bean gum, xanthan gum, gellan gum, and agar.

Preferably, the polymers suitable for use in the present invention include hydroxypropylmethylcellulose (HPMC E15 or HPMC E 5), hydroxypropyl cellulose (HPC), poly (methacrylic acid-co-ethyl acrylate) 1:1 (Eudragit® L 100-55), polyvinylpyrrolidone (PVP K-25, 30, 90; PVP), hydroxypropyl methylcellulose acetate succinate (HPMCAS), pullulan, processed starch, polyethylene oxide (PEO), hydroxyethylcellulose (HEC), hydroxypropyl cellulose (HPC), carboxymethyl cellulose (CMC), polyvinyl alcohol (PVA), polyacrylic acid, methyl methacrylate copolymer, carboxy vinyl polymer, and sodium alginate.

The surfactant used in the present invention mediates bonding between the polymer melt base and amorphous abiraterone acetate produced after the solidification by evaporation. The surfactants suitable for use in the present invention include without limitation anionic surfactants, nonionic surfactants, cationic surfactants, zwitterionic surfactants, and a mixture of one or more thereof.

The surfactants used in the present invention should possess an HLB (Hydrophilic Lipophilic Balance) value of greater than about 2 according to the HLB system which is well known to those skilled in the art. The HLB value provides a means for ranking surfactants according to the balance between the hydrophilic and lipophilic portions of the surfactant agent.

The surfactants suitable for use in the present invention include, but are not limited to, polyoxyethylenealkylaryl ethers such as polyoxyethylene lauryl ether, polyoxyethylenecetyl ether, polyoxyethylenestearyl ether; polyethylene glycol fatty acid esters such as PEG monolaurate, PEG dilaurate, PEG distearate, PEG dioleate; sorbitan fatty acid monoesters; polyoxyethylene castor oil derivates such as polyoxyl hydrogenated castor oil; sodium monooleate, sodium monolaurate, sodium monopalmitate, sodium monostearate, stearylic alcohol, cetostearylic alcohol, polyoxyethylene ricin oil, polyoxyethylene fatty acid glycerides, glycerol fatty acid esters, polyethylene glycol fatty acids esters, polyethylene glycol glycerol fatty acid esters, polyoxyethylene glycerides, lauryl macrogolglycerides, polyoxyethylenesorbitan fatty acid esters, polyoxyethylene vegetable oils, polyoxyethylene hydrogenated vegetable oils; fatty acids, glycerides, tocopherol polyethylene glycol succinates, a triglyceride selected from the group consisting of vegetable oils, fish oils, animal fats, hydrogenated vegetable oils, partially hydrogenated vegetable oils, synthetic triglycerides, modified triglycerides, and fractionated triglycerides. Examples of the anionic surfactants suitable for use in the present invention include, without limitation to sodium deoxycholate, dicetyl phosphate, sodium lauryl sulfate (sodium dodecyl sulfate), sodium cetylstearyl sulfate, sodium dioctylsulfosuccinate (docusate sodium), and the corresponding potassium or calcium salts thereof.

Examples of non-ionic surfactants suitable for use in the present invention include, without limitation to polyoxyl 20 stearate, polyoxyl 40 stearate, polyoxyl 60 stearate, polyoxyl 35 castor oil (Cremophor EL), polyoxyethylenesorbitanmonoisostearate (Tween 20, Tween 80), polyethylene glycol 40 sorbitandiisostearate, polyoxyethyleneoctyl phenyl ether (Triton X100), polyoxyl 40 hydrogenated castor oil (Cremophor® RH 40), polysorbates (polysorbate 20, polysorbate 40, polysorbate 80, polysorbate 85, polysorbate 60), polyoxyethylene fatty acid esters, polyoxyl 40 castor oil, tri block polyoxypropylene (poly(propylene oxide)) polymers (poloxamer 188, poloxamer 407) polyoxyethylenepolyoxypropylene 1800, oleic acid, sorbitan fatty acid monoesters such as sorbitanmonolaurate (Span 20), sorbitanmonooleate (Span 80), sorbitanmonopalmitate (Span 40), sorbitantrioleate (Span 85), sorbitansesquioleate; N-Carbamoylmethoxypolyethylene glycol 2000-1,2-distearol, myristic acid, polyoxyethylene stearates (MYRJ), steareth, sucrose stearate, polyoxyl castor oil, stearic acid, triglyceride synthetic, trimyristin, tristearin, Vitamin E, d-alpha-tocopheryl polyethylene glycol 1000 succinate (TPGS), egg yolk phosphatides, dimyristoylphosphatidylglycerol, dimyristoyl lecithin, propylene glycol monocaprylate (Capryol 90), propylene glycol monocaprylate (Capryol PGMC), deoxycholate, cholesterol, propylene glycol alginate, PEG 60 almond glycerides (Crovol™ A-10), oleoyl macrogol-6 glycerides (Labrafil 1944), linoleoyl macrogol-6 glycerides (Labrafil 2125), caprylocaproyl macrogol-8 glycerides (Labrasol), propylene glycol monolaurate (Lauroglycol 90), propylene glycol laurate (Lauroglycol FCC), calcium stearate, lecithin, Lecithin Centromix E, Lecithin Centrophase 152, Lecithin Central 3F21B, POE (26) glycerine, Olepalisosteariques (PEG-6 isostearate), Pluroldiisostearique (polyglycerol-3-diisostearate), PlurolOleique CC, POE 20 Sorbitantrioleate, polyoxyethylene glycerol trioleate, or macrogol-15 hydroxystearate (Solutol) and a mixture of one or more thereof.

Examples of cationic surfactants suitable for use in the present invention include, but are not limited to quaternary ammonium compounds, such as benzalkonium chloride, benzethonium chloride, cetylpyridinium chloride, cetyltrimethyl ammonium bromide, cetyltrimethyl ammonium chloride, 5-bromo-5-nitro-1,3-dioxane, dimethyldioctadecylammonium chloride, dimethyldioctadecylammonium bromide; and hydrohalide salts of amines, such as octenidinedihydrochloride.

Preferably, the surfactants suitable for use in the present invention include polysorbates, tocopherols (tocopheryl polyethylene glycol 1000 succinate), propylene glycol monocaprylate, caprylocaproyl macrogol-8 glycerides, glycerylcaprylate, poloxamers, PEG-40 hydrogenated castor oil, lecithin, propylene glycol stearates, and polyethylene glycol glycerides.

The plasticizers suitable for use in the present invention include water; citrate esters (eg, triethyl citrate, triacetin); low molecular weight poly (alkylene oxides) (eg, poly (ethylene glycols), poly (propylene glycols), poly (ethylene/propylene glycols)); glycerol, pentaerythritol, glycerol diacetate or triacetate; propylene glycol; and sodium diethylsulphosuccinate.

It should be understood that the plasticizer which can be used in the present invention is not limited to the species mentioned above but can be any compound having the property to enhancing the plastic nature of the material. Preferably, the plasticizers suitable for use in the present invention include polyethylene glycol 300 (PEG 300) polyethylene glycol 400 (PEG 400), polyethylene glycol 600 (PEG 600), polyethylene glycol 1000 (PEG 1000), polyethylene glycol 2000 (PEG 2000), polyethylene glycol 3000 (PEG 3000), polyethylene glycol 4000 (PEG 4000), polyethylene glycol 6000 (PEG 6000), polyethylene glycol 8000 (PEG 8000), polyethylene glycol 10000 to polyethylene glycol 20000, propylene glycol, glycerol, glycerin triacetate, sorbitol, and a mixture of one or more thereof.

The pH modifier suitable for use in the present invention include, without limitation to citric acid, fumaric acid, maleic acid, acetic acid, ascorbic acid, lactic acid, aspartic acid, succinic acid, phosphoric acid, hydrochloric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids and mixtures of one or more thereof. Preferably, the pH modifiers include citric acid, ascorbic acid, and hydrochloric acid.

The disintegrating agents suitable for use in the present invention include without limitation starches, clays, celluloses, algins, gums, cross-linked polymers, crospovidone, croscarmellose sodium, sodium starch glycolate, fully pregelatinized and partially gelatinized, alginates such as calcium alginate and sodium alginate, alginic acid, and magnesium aluminum silicate and mixtures of one or more thereof. Preferably, the disintegrating agent includes crospovidone, croscarmellose sodium, and sodium starch glycolate.

The preservatives suitable for use in the present invention include, without limitation to butylatedhydroxyanisole (BHA), butylatedhydroxytoluene (BHT), ethylenediaminetetraacetic acid (EDTA), methylparaben, propylparaben, sodium benzoate, propyl gallate, and a mixture of one or more thereof. Preferably, the preservatives include butylatedhydroxyanisole, butylatedhydroxytoluene, and propyl gallate.

In some embodiments, the pharmaceutical compositions of the present invention further comprise glidants and/or lubricants selected from the group including, but are not limited to, stearic acid, metallic stearates, zinc stearate, magnesium stearate, magnesium trisilicate, calcium hydroxide, tribasic calcium phosphate, magnesium carbonate, magnesium oxide, calcium stearate, glycerylmonostearate, glycerylbehenate, glycerylpalmitostearate, silicone oil, hydrogenated vegetable oil, hydrogenated castor oil, light mineral oil, mineral oil, polyethylene glycol, methoxypolyethylene glycol, sodium acetate, sodium oleate, sodium chloride, leucine, sodium benzoate, alkyl sulfates, sodium stearylfumarate, talc, colloidal silica, corn starch, powdered cellulose, and/or boric acid.

In some embodiments, the pharmaceutical composition of the present invention further comprises sweetening agents selected from sucralose, saccharin sodium, *glycyrrhiza*, acesulfame, aspartame, *stevia*, neotame, advantame, and a mixture thereof.

In some embodiments, the pharmaceutical composition of the present invention further comprises diluents selected from microcrystalline cellulose, dibasic calcium phosphate anhydrous, isomalt, and a mixture of one or more thereof.

In some embodiments, the pharmaceutical composition of the present invention further comprises flavouring agents selected from the group including, but are not limited to, cherry, strawberry, peppermint, lemon, lemon lime, orange, menthol, vanilla, and a mixture of one or more thereof.

In some embodiments, the pharmaceutical composition of the present invention further comprises coloring agents selected from the group including, but are not limited to, natural organic dyes/lakes, synthetic dyes/lakes. Different types of pigments are distinguished: inorganic pigments, organic pigments, lakes, or pearlescent pigments. Preferably colouring agents include dyes/lakes of yellow, red, orange, blue, titanium dioxide, and a mixture thereof.

In some embodiments, the pharmaceutical composition of the present invention further comprises effervescence agents selected from acidic agents and alkaline agents and a mixture of one or more thereof.

Said acidic agent is a proton donor compound that can react with an alkaline agent which causes the effervescence of the liquid and releases gas.

Suitable acidic agent(s) are selected from tartaric acid, citric acid, maleic acid, fumaric acid, malic acid, adipic acid, succinic acid, lactic acid, glycolic acid, alpha hydroxy acids, ascorbic acid, amino acids, and salts and derivatives of these acids, and mixture thereof.

Suitable alkaline agent(s) selected from potassium carbonate, lithium, sodium, calcium, or ammonium carbonate, L-lysine carbonate, arginine carbonate, sodium glycine carbonate, sodium carbonates of amino acids, sodium bicarbonate (Effer-Soda®), sodium perborate anhydrous, effervescent perborate, sodium perborate monohydrate, sodium percarbonate, sodium dichloroisocyanurate, sodium hypochlorite, calcium hypochlorite and mixtures of one or more thereof.

In another embodiment, the present invention relates to a pharmaceutical composition comprising solid dispersion, wherein said solid dispersion comprises based on the total weight of the composition:
(a) from 2% to 5% by weight amorphous abiraterone acetate;
(b) from 20% to 25% by weight hydroxypropylmethylcellulose;
(c) from 20% to 25% by weight polysorbate 80;
(d) from 0.5% to 2% by weight D-α-tocopheryl polyethylene glycol;
(e) from 10% to 15% by weight propylene glycol monocaprylate;
(f) from 1% to 5% by weight caprylocaproyl macrogol-8 glycerides;
(g) from 15% to 25% by weight polyethylene glycol 8000;
(h) from 5% to 10% by weight polyethylene glycol 400;
(i) from 1% to 3% by weight poly(methacylic acid-co-ethyl acrylate) 1:1;
(j) from 1% to 2% by weight citric acid;
(k) from 3% to 5% by weight croscarmellose sodium; and
(l) from 0.1% to 0.2% by weight butylatedhydroxytoluene;
and optionally comprises one or more excipients selected from sweetening agents, flavouring agents and coloring agents as described herein above.

In another embodiment, the present invention relates to a pharmaceutical composition comprising solid dispersion, wherein said solid dispersion comprises based on the total weight of the composition:
(a) from 2% to 5% by weight amorphous abiraterone acetate;
(b) from 20% to 25% by weight hydroxypropylmethylcellulose;
(c) from 20% to 25% by weight polysorbate 80;
(d) from 0.5% to 2% by weight D-α-tocopheryl polyethylene glycol;
(e) from 10% to 15% by weight propylene glycol monocaprylate;
(f) from 1% to 5% by weight caprylocaproyl macrogol-8 glycerides;
(g) from 15% to 25% by weight polyvinylpyrrolidone;
(h) from 5% to 10% by weight polyethylene glycol 400;
(i) from 1% to 3% by weight poly(methacylic acid-co-ethyl acrylate) 1:1;
(j) from 1% to 2% by weight citric acid;
(k) from 3% to 5% by weight croscarmellose sodium; and
(l) from 0.1% to 0.2% by weight butylatedhydroxytoluene.

The pharmaceutical composition of the present invention can be formulated as dosage forms which include, but are not limited to, powders, granules, pills, tablets, coated tablets, capsules, pellets, patches, implants, films, liquids, semi-solids, gels, aerosols, emulsions, elixirs and the like.

Preferably, the pharmaceutical composition of the present invention can be formulated as oral dosage forms selected from powders, granules, tablets, and capsules, powders for reconstitution, granules for reconstitution.

In another embodiment, the oral dosage include powders for reconstitution and granules for reconstitution.

In another embodiment, capsule and tablets are packed in blisters or bottles.

In another embodiment, the powder or granules are filled in a sachet as final unit dosage package.

In another embodiment, the oral dosage forms comprise abiraterone acetate in an amount ranging from 50 mg to 500 mg, 50 mg to 300 mg, 100 mg to 300 mg, or 200 mg to 300 mg.

Preferably, the oral dosage forms comprising abiraterone acetate in an amount of 50 mg, 100 mg, 150 mg, 200 mg, 250 mg, 300 mg, or 350 mg.

In some embodiments, the pharmaceutical composition of the present invention comprises a range of 70% to 90% of the abiraterone acetate in amorphous form.

In some embodiments, the pharmaceutical composition of the present invention comprises a range of 90% to 99% of the abiraterone acetate in amorphous form.

In some embodiments, the abiraterone acetate is greater than 70% amorphous (i.e., containing less than 30% crystalline abiraterone acetate).

In some embodiments, the abiraterone acetate is greater than 80% amorphous (i.e., containing less than 20% crystalline abiraterone acetate).

In some embodiments, the abiraterone acetate is greater than 90% amorphous (i.e., containing less than 10% crystalline abiraterone acetate).

In some embodiments, the abiraterone acetate is completely amorphous (i.e., containing no crystalline abiraterone acetate).

The present invention also relates to a method for the preparation of the pharmaceutical compositions as described above, wherein said method comprises the steps of:
a) Dissolving abiraterone acetate and pharmaceutically acceptable excipients in a mixture of solvents to form a homogenous solution.
b) Drying the homogenous solution of step (a) at controlled temperatures to get solid dispersion containing amorphous abiraterone acetate.
c) Milling the solid dispersion obtained in step (b) to obtain granules.
d) Optionally mixing and blending the granules obtained in step (c) and one or more pharmaceutically acceptable excipients.
e) Processing the blend obtained in step (d) into pharmaceutical dosage forms.

Suitable solvents that can be used in the present invention are selected from water, acetone, methanol, ethanol, isopropyl alcohol, and a mixture of one or more thereof.

In some embodiments of the present invention, said drying of homogenous solution can be done by casting or pouring the solution and drying at a controlled temperature for evaporation of solvents to form a thin sheet of solid dispersion.

In some embodiments of the present invention, said drying of homogenous solution can be done by pouring in a plate and drying at controlled temperatures for evaporation of solvents to form the solid dispersion.

In some embodiments of the present invention, said drying can be done by forming a thin layer of the solution and drying at a controlled temperature for evaporation of solvents to form the solid dispersion.

In some embodiments of the present invention, said drying can be done by pouring the solution in an open mold and drying at a controlled temperature for evaporation of solvents to form the solid dispersion.

In some embodiments of the present invention, said drying can be done by pouring the solution in a rotary tank and drying at a controlled temperature for evaporation of solvents to form the solid dispersion.

In some embodiments of the present invention, said drying can be done by pouring the solution on a drum and drying at a controlled temperature for evaporation of solvents to form the solid dispersion.

In some embodiments, said drying of homogenous solution can be done by spraying the solution at controlled temperatures for evaporation of solvents to form solid dispersion.

In some embodiments of the present invention, said drying can be done at the temperature less than about 30° C., 35° C., 40° C., 50° C., 60° C., 70° C., 80° C., 90° C., 100° C., 110° C., or 120° C., preferably the drying can be done at a temperature less than about 40° C. or less than about 50° C.

In some embodiments of the present invention, said drying can be done for less than about 1 hr, 2 hr, 3 hr, 4 hr, 5 hr, or 6 hr. preferably, the drying can be done for less than about 3 hr or 5 hr.

In some embodiments of the present invention, the thickness of the sheet can be less than about 400μ, 500μ, 600μ, 700μ, 800μ, 900μ, 1000μ, 1100μ, 1200μ, 1300μ, 1500μ, 1600μ, 1700μ, or 1800μ. Preferably the thickness of the layer can be less than about 500μ, 1000μ, and 1500μ.

In some embodiments of the present invention, said solid dispersion can be brittle, cracked, fragile, fractured, or fissured. Preferably said solid dispersion is fragile and fractured.

In some embodiments of the present invention, said solid dispersion can be milled with an appropriate screen or mesh using a multi mill, hammer mill, knife mill, and ball mill. Preferably the dried material milled with an appropriate screen or mesh using the knife mill.

In some embodiments of the present invention, milled solid dispersion can be in the form of powder, granules, flakes, pellets, or molds.

The compositions disclosed herein comprise abiraterone acetate particles with a median particle size of between 200-800 microns (pm). Such particle size enhances the dissolution rate and consequently the bioavailability.

Another option to evaluate the multimodal particle size distribution (PSD) is by mathematical calculation of D(0.1), D(0.5), and D(0.9) which is performed by calculation of the PSD weighted mean (average) of each of the abiraterone acetate formulations.

In some embodiments of the present invention, the milled solid dispersion having an average mean particle size D (0.5) of from 200μ to 300μ, 200μ to 500μ, 600μ to 700μ, 800μ to 900μ and, 800μ to 1000μ. Preferably the milled solid dispersion having an average mean particle size D (0.5) of from 500μ to 600μ or 600μ to 700μ.

In another embodiment, the total weight of the pharmaceutical composition of the present invention can be in a range from 0.1 grams to 0.5 grams, 0.1 grams to 1 grams, 1 grams to 5 grams, 5 grams to 10 grams, or 7 grams to 10 grams.

In another embodiment, the present invention relates to the pharmaceutical composition comprising solid dispersion of amorphous abiraterone acetate, for use in the treatment of cancers.

In another embodiment, the present invention relates to the pharmaceutical composition comprising solid dispersion of amorphous abiraterone acetate, for use in the treatment of cancer related to 17-α-hydroxylase/C17,20 lyase.

In another embodiment, the present invention relates to the pharmaceutical composition comprising solid dispersion of amorphous abiraterone acetate, for use in the treatment of prostate cancer.

In another embodiment, the present invention relates to the pharmaceutical composition comprising solid dispersion of amorphous abiraterone acetate, for use in the treatment of non-metastatic castration-resistant prostate cancer.

In another embodiment, the present invention relates to the pharmaceutical composition comprising solid dispersion of amorphous abiraterone acetate, for use in the treatment of metastatic castration-resistant prostate cancer.

In another embodiment, the present invention relates to the pharmaceutical composition comprising solid dispersion of amorphous abiraterone acetate, for use in the treatment of non-metastatic castration-sensitive prostate cancer.

In another embodiment, the present invention relates to the pharmaceutical composition comprising solid dispersion of amorphous abiraterone acetate, for use in the treatment of metastatic castration-sensitive prostate cancer.

In yet another aspect, the present invention relates to the pharmaceutical composition comprising solid dispersion of amorphous abiraterone acetate, for use in the treatment of breast cancer. In yet another aspect, the present invention relates to the pharmaceutical composition comprising solid dispersion of amorphous abiraterone acetate, for use in the treatment of ovarian cancer.

In yet another aspect, the present invention relates to the pharmaceutical composition comprising solid dispersion of amorphous abiraterone acetate, for use in the treatment of cancer related to 17-α-hydroxylase/C17,20 lyase in combination with glucocorticoids.

In yet another aspect, the present invention relates to the pharmaceutical composition comprising solid dispersion of amorphous abiraterone acetate, for use in the treatment of metastatic castration-resistant prostate cancer in combination with a glucocorticoid.

In yet another aspect, the present invention relates to the pharmaceutical composition comprising solid dispersion of amorphous abiraterone acetate, for use in the treatment of metastatic castration-sensitive prostate cancer in combination with a glucocorticoid.

Examples of glucocorticoids include, but are not limited to, prednisone, prednisolone, methylprednisolone, beclomethasone, betamethasone, budesonide, cortisone, dexamethasone, hydrocortisone, and triamcinolone.

In yet another embodiment, the present invention relates to a method of treating cancer relates to 17-α-hydroxylase/C17,20 lyase, comprising administering to the patient therapeutically effective amount of the pharmaceutical composition described herein.

In another embodiment, the pharmaceutical composition of the present invention can be administered 1 to 3 times per day, based on the condition of the subject.

In yet another embodiment, the pharmaceutical composition of the present invention can be administered to a patient directly or with soft foods or by dissolving in water.

ABBREVIATIONS

AUC: Area under the curve
$C_{max}$: Maximum plasma concentration
DSC: Differential Scanning Calorimetry
FaSSIF: Fasted State Simulated Intestinal Fluid
FeSSIF: Fed State Simulated Intestinal Fluid
g: Grams
HDPE: High density polyethylene
HPLC: High performance liquid chromatography
hr: Hours
kg: Kilogram
LC-MS/MS: Liquid chromatography/Tandem mass spectrometry
mg: Milligram
min: Minutes
mL: Milliliter
ng: Nanogram
N: Normality
PK: Pharmacokinetic
PSD: Particle Size Distribution
*Q.S: Quantity Sufficient
RPM: Rotation Per Minute
RMG: Rapid Mixer Granulator
RH: Relative Humidity
RLD: Reference Listed Drug
$T_{max}$: Time of maximum plasma concentration
$T_{1/2}$: Half-life
° C.: Degree Celsius
USP: United States Pharmacopoeia
% W/W: Percent weight/weight
XRD: X-Ray Powder Diffraction
%: Percentage
CV: Coefficient of Variation
μL: Microlitre
μ: Microns ng/mL Nanogram/mililitre

EXAMPLES

The following Examples are provided to illustrate preferred embodiments of the invention and are not intended to limit the scope of the present invention.

Method for the Preparation of Pharmaceutical Composition:

Method for the preparation of the pharmaceutical composition comprises solid dispersion of amorphous abiraterone acetate and one or more pharmaceutically acceptable excipients, said method comprising the steps of:
a. Dissolving abiraterone acetate with one of the surfactant to get a homogenous solution.
b. Adding polymers and other surfactants to step a) to get a clear homogenous solution.
c. Finally adding pH modifier, disintegrant, and preservative to step b) by mixing to get a homogenous solution.
d. Drying the homogenous solution of step c) by casting and drying at controlled temperatures to get solid dispersion of amorphous abiraterone acetate.
e. Milling the solid dispersion obtained in step d) to get fine granules.
f. Optionally mixing and blending the granules obtained in step e) and one or more pharmaceutically acceptable excipients.
g. Processing the blend obtained in step f) into dosage forms such as powders, capsules, tablets, granules, and the like.

Example 1: Preparation of Granules Comprising Solid Dispersion of Amorphous Abiraterone Acetate

| S. No | Ingredients | Quantity (% w/w) |
|---|---|---|
| 1 | Abiraterone acetate | 2.84 |
| 2 | Hydroxypropylmethylcellulose (HPMC E15) | 24.08 |
| 3 | Polysorbate 80 (Tween ® 80) | 24.08 |
| 4 | D-α-tocopheryl polyethylene glycol (TPGS) | 0.91 |
| 5 | Propylene glycol monocaprylate (Capryol ™ 90) | 12.23 |
| 6 | Caprylocaproyl macrogol-8 glycerides (Labrasol ®) | 2.61 |
| 7 | Citric acid | 1.14 |
| 8 | Croscarmellose sodium (CCS) | 4.09 |
| 9 | Butylatehydroxytoluene (BHT) | 0.09 |
| 10 | Polyethylene glycol 8000 (PEG 8000) | 20.44 |
| 11 | Polyethylene glycol 400 (PEG 400) | 7.50 |
| 12 | Ethanol | *Q.S |
| 13 | Purified water | *Q.S |
|  | Total | 100 |

250 mg of abiraterone acetate equivalent formulation was prepared

Preparation: Crystalline abiraterone acetate was dissolved in Tween®80 to get a homogenous solution; polymer (HPMC) was added to the obtained homogenous solution; the above solution was dissolved in 9:1 (ethanol:water) along with remaining surfactants (Capryol™ 90, Labrasol® and TPGS) and plasticizers (PEG 400 & PEG 8000) to get clear homogenous solution upon mixing, further pH modifier (citric acid), disintegrating agent (CCS) and preservative (BHT) were added while mixing to get a homogenous solution; finally the obtained homogenous solution was poured on a sheet and dried at temperature 40° C. for 1 hr to evaporate solvent; further drying carried out for 2 hr at a temperature 40° C. using tray dryer to get solid dispersion of amorphous abiraterone acetate. The dried solid dispersion was milled using knife mill to get granules.

Examples 2 and 3: The granules compositions of examples 2 and 3 were prepared by following the preparation procedure as described in example 1, with some non-critical variations.

| S. No | Ingredients | Example 2 (% w/w) | Example 3 (% w/w) |
|---|---|---|---|
| 1 | Abiraterone acetate | 5.52 | 8.06 |
| 2 | Hydroxypropyl-methylcellulose (HPMC E15) | 23.41 | 22.78 |
| 3 | Polysorbate 80 (Tween ® 80) | 23.41 | 22.78 |
| 4 | D-α-tocopheryl polyethylene glycol (TPGS) | 0.88 | 0.86 |
| 5 | Propylene glycol monocaprylate (Capryol ™ 90) | 11.89 | 11.57 |
| 6 | Caprylocaproyl macrogol-8 glycerides (Labrasol ®) | 2.54 | 2.47 |
| 7 | Citric acid | 1.10 | 1.07 |
| 8 | Croscarmellose sodium (CCS) | 3.97 | 3.89 |
| 9 | Butylatedhydroxytoluene (BHT) | 0.11 | 0.08 |
| 10 | Polyethylene glycol 8000 (PEG 8000) | 19.88 | 19.35 |
| 11 | Polyethylene glycol 400 (PEG 400) | 7.29 | 7.09 |
| 12 | Ethanol | *Q.S | *Q.S |
| 13 | Purified water | *Q.S | *Q.S |
|  | Total | 100 | 100 |

250 mg of abiraterone acetate equivalent formulation was prepared

Examples 4 to 6: The granules compositions of examples 4 to 6 were prepared by following the preparation procedure as described in example 1, with some non-critical variations.

| S. No | Ingredients | Example 4 (% w/w) | Example 5 (% w/w) | Example 6 (% w/w) |
|---|---|---|---|---|
| 1 | Abiraterone acetate | 10.47 | 12.75 | 20.31 |
| 2 | Hydroxypropylmethylcellulose (HPMC E15) | 22.19 | 21.62 | 19.75 |
| 3 | Polysorbate 80 (Tween ® 80) | 22.19 | 21.62 | 19.75 |
| 4 | D-α-tocopheryl polyethylene glycol (TPGS) | 0.84 | 0.82 | 0.75 |
| 5 | Propylene glycol monocaprylate (Capryol ™ 90) | 11.27 | 10.98 | 10.03 |
| 6 | Caprylocaproyl macrogol-8 glycerides (Labrasol ®) | 2.41 | 2.35 | 2.14 |
| 7 | Citric acid | 1.05 | 1.02 | 0.93 |
| 8 | Croscarmellose sodium (CCS) | 3.77 | 3.67 | 3.35 |
| 9 | Butylatedhydroxytoluene (BHT) | 0.08 | 0.08 | 0.07 |
| 10 | Polyethylene glycol 8000 (PEG 8000) | 18.84 | 18.36 | 16.77 |
| 11 | Polyethylene glycol 400 (PEG 400) | 6.91 | 6.73 | 6.15 |
| 12 | Ethanol | *Q.S | *Q.S | *Q.S |
| 13 | Purified water | *Q.S | *Q.S | *Q.S |
|  | Total | 100 | 100 | 100 |

250 mg of abiraterone acetate equivalent formulation was prepared

Examples 7 to 9: The granules compositions of examples 7 to 9 were prepared by following the preparation procedure as described in example 1, with some non-critical variations.

| S. No. | Ingredients | Example 7 (% w/w) | Example 8 (% w/w) | Example 9 (% w/w) |
|---|---|---|---|---|
| 1 | Abiraterone acetate | 3.15 | 3.06 | 3.10 |
| 2 | Hydroxypropylmethylcellulose (HPMC E15) | 22.98 | — | 22.60 |
| 3 | Hydroxypropylmethylcellulose (HPMC E 5) | — | 22.36 | — |
| 4 | Polysorbate 80 (Tween ® 80) | 23.83 | 23.19 | 23.44 |
| 5 | D-α-tocopheryl polyethylene glycol (TPGS) | 0.90 | 0.88 | 0.88 |
| 6 | Propylene glycol monocaprylate (Capryol ™ 90) | 12.11 | — | — |
| 7 | Glycerylcaprylate (Capmul ® MCM) | — | 11.78 | 11.90 |
| 8 | Caprylocaproyl macrogol-8 glycerides (Labrasol ®) | 2.59 | 2.52 | 2.54 |
| 9 | Citric acid | 1.12 | 1.09 | 1.11 |
| 10 | Croscarmellose sodium (CCS) | 4.05 | 3.94 | — |
| 11 | Sodium starch glycolate | — | — | 3.98 |
| 12 | Butylatedhydroxytoluene (BHT) | 0.11 | 0.11 | 0.11 |
| 13 | Colloidal silicon dioxide (Aerosil ®) | — | 1.64 | 1.66 |
| 14 | Polyethylene glycol 8000 (PEG 8000) | 20.23 | 19.67 | 19.9 |
| 15 | Polyethylene glycol 400 (PEG 400) | 7.42 | 7.22 | 7.30 |
| 16 | Poly(methacrylic acid-co-ethyl acrylate) 1:1 (Eudragit ® L 100-55) | 1.51 | 1.47 | — |
| 17 | Hydroxypropyl methylcellulose acetate succinate (HPMCAS) | — | — | 1.48 |
| 18 | Polyvinylpyrrolidone (PVP K-30) | — | 1.07 | — |
| 19 | Ethanol:Water (9:1) | *Q.S | *Q.S | *Q.S |
|  | Total | 100 | 100 | 100 |

250 mg of abiraterone acetate equivalent formulation was prepared

Examples 10 to 12: The granules compositions of examples 10 to 12 were prepared by following the preparation procedure as described in example 1, with some non-critical variations.

| S. No. | Ingredients | Example 10 (% w/w) | Example 11 (% w/w) | Example 12 (% w/w) |
|---|---|---|---|---|
| 1 | Abiraterone acetate | 3.10 | 3.10 | 3.10 |
| 2 | Hydroxypropyl-methylcellulose (HPMC E15) | 22.60 | — | 22.60 |
| 3 | Hydroxypropyl-methylcellulose (HPMC E 5) | — | 22.60 | — |
| 4 | Polysorbate 80 (Tween ® 80) | 23.44 | 23.44 | 23.44 |
| 5 | D-α-tocopheryl polyethylene glycol (TPGS) | 0.88 | 0.88 | 0.88 |
| 6 | Glycerylcaprylate (Capmul ® MCM) | 11.90 | 11.90 | 11.90 |
| 7 | Caprylocaproyl macrogol-8 glycerides (Labrasol ®) | 2.54 | 2.54 | 2.54 |
| 8 | Citric acid | 1.11 | 1.11 | 1.11 |
| 9 | Croscarmellose sodium (CCS) | 3.98 | 3.98 | 3.98 |
| 10 | Butylatedhydroxytoluene (BHT) | 0.11 | 0.11 | 0.11 |
| 11 | Colloidal silicon dioxide (Aerosil ®) | 1.66 | 1.66 | 1.66 |
| 12 | Poloxamer 188 | — | 19.90 | — |
| 13 | Polyethylene glycol 8000 (PEG 8000) | 19.9 | — | 19.9 |
| 14 | Polyethylene glycol 400 (PEG 400) | 7.30 | 7.30 | 7.30 |
| 15 | PEG-40 Hydrogenated Castor Oil (Cremophor ® RH40) | — | — | 1.48 |

| S. No. | Ingredients | Example 10 (% w/w) | Example 11 (% w/w) | Example 12 (% w/w) |
|---|---|---|---|---|
| 16 | Polyvinylpyrrolidone | 1.48 | 1.48 | — |
| 17 | Ethanol:Water (9:1) | *Q.S | *Q.S | *Q.S |
|  | Total | 100 | 100 | 100 |

250 mg of abiraterone acetate equivalent formulation was prepared

Examples 13 to 15: The granules compositions of examples 13 to 15 were prepared by following the preparation procedure as described in example 1, with some non-critical variations.

| S. No. | Ingredients | Example 13 (% w/w) | Example 14 (% w/w) | Example 15 (% w/w) |
|---|---|---|---|---|
| 1 | Abiraterone acetate | 3.14 | 3.14 | 3.00 |
| 2 | Hydroxypropylmethyl cellulose (HPMC E15) | 22.95 | 22.95 | 23.01 |
| 3 | Polysorbate 80 (Tween ® 80) | 23.81 | 23.81 | 23.87 |
| 4 | D-α-tocopheryl polyethylene glycol (TPGS) | 0.90 | 0.90 | 0.90 |
| 5 | Propylene glycol monocaprylate (Capryol™ 90) | 12.09 | 12.09 | 12.13 |
| 6 | Caprylocaproyl macrogol-8 glycerides (Labrasol ®) | 2.58 | 2.58 | 2.59 |
| 7 | Citric acid | 1.12 | 1.12 | 1.13 |
| 8 | Croscarmellose sodium (CCS) | 4.04 | 4.04 | 4.05 |
| 9 | Butylated-hydroxytoluene (BHT) | 0.11 | 0.11 | 0.11 |
| 10 | Polyethylene glycol 8000 (PEG 8000) | 20.21 | 20.21 | — |
| 11 | Polyethylene glycol 400 (PEG 400) | 7.44 | 7.44 | 7.43 |
| 12 | Propyl gallate | 0.11 | — | — |
| 13 | Butylated-hydroxyanisole (BHA) | — | 0.11 | — |
| 14 | Poly(methacrylic acid-co-ethyl acrylate) 1:1 (Eudragit ® L 100-55) | 1.5 | 1.5 | 1.51 |
| 15 | Polyvinylpyrrolidone (PVP K25) | — | — | 20.27 |
| 16 | Ethanol:Water (9:1) | *Q.S | *Q.S | *Q.S |
|  | Total | 100 | 100 | 100 |

250 mg of abiraterone acetate equivalent formulation was prepared

Example 16: The granules compositions of example 16 were prepared by following the preparation procedure as described in example 1, followed by the addition of sweeteners, flavoring agent, and coloring agent with some non-critical variations.

| S. No | Ingredients | Quantity (% w/w) | Quantity (mg) |
|---|---|---|---|
| 1 | Abiraterone acetate | 3.00 | 250.00 |
| 2 | Hydroxypropylmethylcellulose (HPMC E15) | 21.14 | 1760.01 |
| 3 | Polysorbate 80 (Tween ® 80) | 21.93 | 1825.87 |
| 4 | D-α-tocopheryl polyethylene glycol (TPGS) | 0.83 | 68.97 |
| 5 | Propylene glycol monocaprylate (Capryol™ 90) | 11.14 | 927.59 |
| 6 | Caprylocaproyl macrogol-8 glycerides (Labrasol ®) | 2.38 | 198.28 |
| 7 | Citric acid | 1.03 | 86.04 |
| 8 | Croscarmellose sodium (CCS) | 3.72 | 309.66 |
| 9 | Butylated hydroxytoluene (BHT) | 0.11 | 9.48 |
| 10 | Polyethylene glycol 8000 (PEG 8000) | 18.63 | 1550.01 |
| 11 | Polyethylene glycol 400 (PEG 400) | 6.83 | 568.62 |
| 12 | Poly(methacrylic acid-co-ethyl acrylate) 1:1 (Eudragit ® L 100-55) | 1.39 | 115.52 |
| 13 | Neotame | 0.21 | 17.24 |
| 14 | Sucralose | 3.72 | 309.48 |
| 15 | Orange flavor | 3.93 | 326.73 |
| 16 | Sunset yellow | 0.01 | 0.86 |
| 17 | Ethanol:Water (9:1) | *Q.S | *Q.S |
|  | Total | 100.0 | 8324.37 |

Example 16 comprising abiraterone acetate granules sere analyzed to detect particle size distribution using laser diffraction method (Malvern Mastersizer S); and mathematical calculation of d(0.1), d(0.5), and d(0.9) by the calculation of the PSD weighted mean (FIG. 6).

Example 17: Granules Compositions Comprising Effervescence Mixture of Sodium Bicarbonate and Citric Acid

| Ingredients | Quantity (% w/w) | Quantity (mg) |
|---|---|---|
| Abiraterone acetate Granules of example 7 (250 mg of abiraterone acetate) | 93.4 | 7,797.13 |
| Sodium bicarbonate (Effer-Soda ®) | 4.1 | 368.38 |
| Citric acid | 2.5 | 221.38 |
| Total | 100% | 8,386.89 mg |

Preparation: Granules obtained in example 7 were milled and blended with Effer-Soda®, citric acid, and processed the blend obtained into free flowing granules.

Example 18: Capsules Comprising Abiraterone Acetate Granules

Abiraterone acetate capsules were prepared with and without processing of granular material from examples 1 to 16. Preparation: Required quantity of the granules obtained in examples 1 to 16 was passed through #20 mesh. Separately taken dispensed quantity of glidant such as silica, starch, aluminum silicates, calcium silicate, sodium stearylfumarate or magnesium stearate, was passed through #40 mesh; obtained glidant was added to the granules to reduce agglomeration and/or to aid flow of granules during capsule filling. Both the materials were introduced and mixed in octagonal blender for 10 min. The final blend obtained was filled into capsules.

Example 19: Preparation of Abiraterone Acetate Tablets

The granules obtained in examples 1 to 16 were utilized for the preparation of tablet formulation using fillers such as diluents, disintegrating agents, lubricants, glidants, etc.

| Ingredients | Quantity (% w/w) | Quantity (mg/Tablet) |
|---|---|---|
| Abiraterone acetate Granules (Examples 1 to 16) | 75 | 750 |
| Colloidal silicon dioxide (Aerosil ® 200) | 5 | 50 |
| Dibasic Calcium Phosphate Anhydrous (Fujicalin ®) | 9 | 90 |
| Crospovidone(Kollidon ® CL-F) | 10 | 100 |
| Magnesium stearate | 1 | 10 |
| Total | 100% | 1100.00 mg |

Preparation:
  a) Dispensed quantity of the granules was sifted through #20 mesh.
  b) Dispensed quantity of glidant (Aerosil®200) was sifted through #40 mesh.
  c) Materials obtained in step (a) and step (b) were mixed in a polybag for 5 min.
  d) Dispensed quantity of Kollidon® CL-F, and Fujicalin® was sifted through #40 ASTM sieve.
  e) Materials obtained in step (c) and step (d) were mixed in a blender for 5 min.
  f) Dispensed quantity of lubricant (Magnesium stearate or Sodium Stearylfumarate) was sifted through #40 mesh and mixed with materials of step (e) in a blender for 2 min to get a blend.
  g) Finally, the blend obtained from step (f) was compressed at tablets weight of 1100 mg using Eliza press automatic rotary compression machine with tablet size of 19.0×9.5 mm Oval-shaped, standard concave dies, and punches (D-Tooling).
  h) The ratio of granules and other excipients was maintained at a ratio of 66:34, 70:30, and 75:25. Eg. 75% of granules of each dose were compressed with 2500 fillers as mentioned in steps (a) to (g) for tablet compression.

Examples 20 and 21: Tablets of examples 20 and 21 were prepared by following the procedure as described in example 19, with some non-critical variations.

Example 20: Tablets Comprising Abiraterone Granules Obtained in Examples 1 to 16

| Ingredients | Quantity (% w/w) | Quantity (mg/Tablet) |
|---|---|---|
| Abiraterone acetate Granules (Example 1 to 16) | 70 | 700 |
| Aerosil ® 200 | 5 | 50 |
| Fujicalin ® | 14 | 140 |
| Kollidon ® CL-F | 10 | 100 |
| Sodium Stearylfumarate | 1 | 10 |
| Total | 100% | 1100 mg |

Example 21: Tablets Comprising Abiraterone Granules Obtained in Examples 1 to 16

| Ingredients | Quantity (% w/w) | Quantity (mg/Tablet) |
|---|---|---|
| Abiraterone acetate Granules (Example 1 to 16) | 66 | 726 |
| Aerosil ® 200 | 5 | 55 |
| Avicel ® PH 102 | 10 | 110 |
| Fujicalin ® | 10 | 110 |
| Kollidon ® CL-F | 8 | 88 |
| Magnesium stearate | 1 | 11 |
| Total | 100% | 1100 mg |

The placebo formulation for examples 1 to 21 was used as a control during the physical and chemical evaluation study. The manufacturing process is similar to the abiraterone acetate containing formulations with some non-critical variations.

Example 22: Dissolution Studies

Dissolution studies were performed to compare the dissolution rate of the pharmaceutical composition disclosed in the present invention with the currently marketed product, Zytiga® (250 mg).

Dissolution properties of examples 1 to 16 were assessed using USP type-2 dissolution apparatus at temperature 37° C. in biorelevant media, simulated fasted state intestinal media (FaSSIF), simulated fed state intestinal media (FeSSIF), at a stirring rate of 100 rpm at a concentration of 0.5 mg/mL strength. Samples were collected at 10, 20, and 30 min time points. The percent (0%) abiraterone acetate release was measured using TIPLC method.

Dissolution data of Zytiga® and examples 1 to 16 are given in the table below.

TABLE 1

Dissolution study data of examples 1 to 16 compared to Zytiga ®.

| | % Released Time (min) | | | | | |
|---|---|---|---|---|---|---|
| | FaSSIF | | | FeSSIF | | |
| Examples/Zytiga ® | 10 | 20 | 30 | 10 | 20 | 30 |
| Zytiga ® 250 mg/Tablet | 1.9 | 2.7 | 3.1 | 15.3 | 17.9 | 18.7 |
| Example 1 | 61.8 | 66.6 | 67.1 | 74.0 | 89.2 | 89.1 |
| Example 2 | 20.1 | 22.8 | 21.2 | 35.8 | 38.5 | 37.0 |
| Example 3 | 14.9 | 14.8 | 13.6 | 26.8 | 27.7 | 27.3 |
| Example 4 | 13.5 | 12.7 | 11.1 | 25.3 | 26.0 | 24.4 |
| Example 5 | 10.6 | 9.7 | 8.7 | 23.8 | 24.0 | 24.3 |
| Example 6 | 5.4 | 7.1 | 6.9 | 18.3 | 22.2 | 22.7 |
| Example 7 | 23.7 | 37.5 | 50.8 | 29.3 | 49.0 | 71.2 |
| Example 8 | 69.4 | 75.2 | 74.1 | 61.3 | 70.0 | 68.0 |
| Example 9 | 73.4 | 74.2 | 72.1 | 70.4 | 77.9 | 75.5 |
| Example 10 | 83.2 | 83.8 | 81.6 | 91.3 | 97.1 | 94.6 |
| Example 11 | 85.9 | 87.0 | 85.4 | 94.8 | 96.3 | 83.3 |
| Example 12 | 85.0 | 85.3 | 92.7 | 92.9 | 94.3 | 92.6 |
| Example 13 | 86.8 | 86.8 | 85.5 | 77.6 | 82.3 | 61.7 |
| Example 14 | 55.4 | 59.2 | 81.7 | 74.9 | 77.4 | 79.8 |
| Example 15 | 68.5 | 80.4 | 80.4 | 52.8 | 65.6 | 68.5 |
| Example 16 | 26.8 | 52.3 | 71.5 | 27.8 | 55.1 | 72.3 |

Conclusion: Granules composition of examples 1 to 16 showed greater release of abiraterone acetate under FaSSIF and FeSSIF media compared to the marked product, Zytiga® (250 mg).

Example 25: Stability

The stability studies were carried out by evaluating impurity levels in the pharmaceutical compositions disclosed herein.

Protocol: The pharmaceutical compositions of the present invention were stored at accelerated storage condition (i.e., temperature 40±2° C. at 75±5% relative humidity (RH)) and long term storage condition (25° C.±2° C./75%±5% RH); impurities were measured by using HPLC. Stability data are given in the below tables.

TABLE 2

Stability of the pharmaceutical composition disclosed herein under accelerated storage condition on day one.

| S. No. | Example number | Purity (%) | Known Impurity (%) |
|---|---|---|---|
| 1 | Example 1 | 99.84 | 0.10 |
| 2 | Example 2 | 99.87 | 0.07 |
| 3 | Example 3 | 99.89 | 0.06 |
| 4 | Example 4 | 99.90 | 0.05 |
| 5 | Example 5 | 99.90 | 0.05 |
| 6 | Example 6 | 99.91 | 0.04 |
| 7 | Example 8 | 99.59 | 0.34 |
| 8 | Example 9 | 99.68 | 0.22 |
| 9 | Example 10 | 99.43 | 0.49 |
| 10 | Example 11 | 99.76 | 0.18 |
| 11 | Example 12 | 99.73 | 0.20 |
| 12 | Example 13 | 99.62 | 0.24 |
| 13 | Example 14 | 99.70 | 0.21 |

TABLE 3

Stability of the pharmaceutical composition disclosed herein under accelerated storage condition at end of the one month.

| S. No. | Example number | Purity (%) | Known Impurity (%) |
|---|---|---|---|
| 1 | Example 1 | 99.35 | 0.43 |
| 2 | Example 2 | 99.59 | 0.28 |
| 3 | Example 3 | 99.66 | 0.19 |
| 4 | Example 4 | 99.75 | 0.18 |
| 5 | Example 5 | 99.70 | 0.22 |
| 6 | Example 6 | 99.74 | 0.14 |
| 7 | Example 8 | 99.32 | 0.57 |
| 8 | Example 9 | 99.42 | 0.35 |
| 9 | Example 10 | 97.82 | 1.89 |
| 10 | Example 11 | 99.24 | 0.63 |
| 11 | Example 12 | 99.28 | 0.50 |
| 12 | Example 13 | 98.95 | 0.76 |
| 13 | Example 14 | 99.02 | 0.75 |

TABLE 4

Stability of the pharmaceutical composition of example 16 at accelerated storage condition over the period of six months.

| Number of Days | Purity (%) | Known Impurity (%) |
|---|---|---|
| Day one | 99.68 | 0.15 |
| One month | 99.28 | 0.62 |
| Three months | 98.08 | 1.76 |
| Six months | 95.37 | 4.51 |

TABLE 5

Stability of the pharmaceutical composition of example 15 at long term storage condition (25° C. ± 2° C./75% ± 5% RH) over the period of six months.

| Storage period | Purity (%) | Known Impurity (%) |
|---|---|---|
| Day one | 99.93 | 0.03 |
| Sixmonths | 99.13 | 0.83 |

TABLE 6

Stability of the pharmaceutical composition of example 7 at long term storage condition (25° C. ± 2° C./75% ± 5% RH) over the period of fourteen months.

| Storage period | Purity (%) | Known Impurity (%) |
|---|---|---|
| Day one | 99.68 | 0.15 |
| Sixmonths | 98.92 | 0.99 |
| Fourteen months | 97.71 | 2.16 |

Abiraterone acetate composition of the present invention was characterized for known impurities of abiraterone, 7-keto abiraterone acetate, α-epoxy abiraterone acetate, abiraterone ethyl ether. The major known impurity i.e., abiraterone is mentioned above in tables 2 to 6. Unknown impurities are not detected.

Example 26: Characterization by XRD

X-ray Diffraction (XRD) was performed by PanalyticalX'pert Proto detect the presence of amorphous abiraterone acetate in the pharmaceutical solid dispersion composition disclosed herein, compared to crystalline abiraterone acetate and placebo. Samples are tested by using CuKa radiation (1=1.542 A), excitation voltage: 45 kV, anode current: 40 mA, measuring range: 5-50° 2θ, step size: 0.02° scattering angle. Diffraction signals are processed by Highscore plus software. Placebo and active formulation have similar XRD patterns. The resulted data confirms the formation of amorphous abiraterone acetate in the present pharmaceutical compositions compared to crystalline abiraterone acetate and placebo (FIGS. 1 to 5).

X-ray diffraction of the pharmaceutical composition for example 16 and 15 of the present invention at accelerated storage condition (40° C./75% RH) and long term storage condition (25° C./60% RH) for six months showed similar diffraction patterns compared to placebo (FIGS. 4 and 5).

Example 27: In-Vivo Pharmacokinetic Study

Pharmacokinetic (PK) evaluation of abiraterone acetate granules of example 7 and 16 (equivalent to 50 mg abiraterone acetate) compared to Zytiga® (250 mg tablet of abiraterone acetate) following a single oral administration to male Beagle dogs.

Male Beagle dogs (9.0-12 kg) were used as experimental animals. Example 7 formulation was conducted in two-way cross-over, comparative pharmacokinetic (PK) study following a single oral administration of abiraterone granules (each capsule contains 12.5 mg of abiraterone acetate filled in capsule/equivalent to 50 mg abiraterone acetate/dog); performed under fasted and fed condition to male Beagle dogs. Whereas Example 16 was dosed into a separate set of animals under fasting conditions. Reference listed drug (RLD), Zytiga® (250 mg abiraterone acetate tablet) was also evaluated under fasted and fed condition in a two-way cross-over study for comparison purposes. A minimum of 15 days washout period was given between each period. Each dog was dosed a single oral administration, with the tablet/capsule was placed on the back of the tongue and the throat was massaged for swallowing of tablet/capsule. Immediately 50 mL of drinking water was administered via syringe to ensure the tablet/capsule was washed down into the stomach.

Fasted conditions: Animals were fasted overnight before dosing with ad libitum access to drinking water. Post-dose animals were fasted for another 4 hr. Animals were deprived of water for 1 hr pre and post dose.

Fed conditions (Food effect study): Approximately 55 g of in-house prepared high fat diet (based on FDA guidelines) was given at 10 min prior to dosing a tablet/capsule. Regular feed was offered at 4 hr post-dose. Animals were deprived of water for 1 hr pre and post dose.

At pre-determined point, blood samples were collected through cephalic/saphenous vein. Blood samples were collected at following time points: pre-dose, 0.25, 0.5, 0.75, 1, 1.5, 2, 3, 4, 6, 8, 12 and 24 hr post dose. Collected blood was transferred into labeled micro centrifuge tubes containing 10 µL of heparin as an anticoagulant and centrifuged at 4000 rpm for 10 min. Plasma was separated and stored frozen at −80° C. until analysis. The concentrations of the abiraterone were quantified in plasma by qualified LC-MS/MS method using a suitable extraction technique. The abiraterone was quantified in the calibration range around 1.0-500 ng/mL in plasma. Study samples were analyzed using calibration samples in the batch and quality control samples spread across the batch.

PK parameters $C_{max}$, $T_{max}$, $AUC_{last}$, and $T_{1/2}$ were calculated by non-compartmental model using standard non-compartmental model by using Phoenix WinNonlin 8.1 version Software package. The area under the plasma concentration-time curve (AUC) was calculated by the linear trapezoidal method. Relative bioavailability of the test formulations as compare to the Zytiga® was calculated as the ratio of AUC of test formulation/AUC of Zytiga® tablets, adjusted for the difference in doses, and is presented in the final column of Table 7. Relative exposures for food effect ($AUC_{fed}/AUC_{fasted}$) were calculated for test and Zytiga® tablets and are presented in the final column of Table 8.

TABLE 7

PK comparative data of abiraterone acetate granules of example 7 and 16 (equivalent to 50 mg, abiraterone acetate) against Zytiga ® (250 mg tablet, abiraterone acetate) following a single oral administration to male Beagle dogs.

| Formulation | Feeding condition | Dose (mg) | $T_{max}$ (h) | $T_{1/2}$ (h) | $C_{max}$ (ng/mL) | $AUC_{last}$ (h•ng/mL) | F Value (Dose adjusted) (unitless) |
|---|---|---|---|---|---|---|---|
| Zytiga ® | Fasted | 250 | 1.25 (0.5-3) | 2.72 ± 1.85 (68) | 123 ± 97.5 (79) | 263 ± 271 (103) | 1 |
| Example 7 | Fasted | 50 | 1 (0.75-1.5) | 2.66 ± 1.12 (42) | 243 ± 87.7 (36) | 371 ± 96.8 (26) | 7.1 |
| Example 16 | Fasted | 50 | 0.50 (0.25-0.50) | 5.78 ± 3.42 (59) | 233 ± 125 (54) | 306 ± 153 (50) | 5.8 |

Number of animals = 6 dogs/formulation;
Values are Mean ± Standard deviation, Coefficient of Variation (% CV);
$T_{max}$ values are given as median (min-max).

Results: PK analysis was performed comparing the abiraterone granule formulations (examples 7 and 16) to the Zytiga® reference tablet. The PK parameters are presented in Table 7. PK analysis comparing abiraterone granules of Examples 7 and 16 to Zytiga® established the athematic mean ratios of dose-normalized $AUC_{last}$ to be 7.1 and 5.8, respectively. Overall, examples 7 and 16 granule formulations were able to enhance the bioavailability of abiraterone by 7.1 and 5.8 fold respectively, as compared to Zytiga® tablet formulation in dogs. This result signifies a substantial improvement in the bioavailability of abiraterone generated by a composition of the current invention over the commercial product, Zytiga®.

TABLE 8

Comparative pharmacokinetics of abiraterone acetate granules (example 7) versus Zytigain ® fasted/fed male Beagle dogs following a single oral dose.

| Formulation | Feeding condition | Dose (mg) | $T_{max}$ (h) | $T_{1/2}$ (h) | $C_{max}$ (ng/mL) | $AUC_{last}$ (h•ng/mL) | Food effect (fed/fasted) |
|---|---|---|---|---|---|---|---|
| Zytiga ® | Fasted | 250 | 1.25 (0.5-3) | 2.72 ± 1.85 (68) | 123 ± 98 (79) | 263 ± 271 (103) | — |
| Zytiga ® | Fed, high fat | 250 | 1 (1-1) | 7.13 ± 2.13 (30) | 997 ± 301 (30) | 1865 ± 514 (28) | 7.1 |
| Example 7 | Fasted | 50 | 1 (0.75-1.5) | 2.66 ± 1.12 (42) | 243 ± 88 (36) | 371 ± 96.8 (26) | — |
| Example 7 | Fed, high fat | 50 | 1.5 (1.5-2) | 5.45 ± 3.36 (62) | 213 ± 41 (19) | 364 ± 75 (21) | 0.98 |

Number of animals = 6 dogs/formulation;
Values are Mean ± Standard deviation, Coefficient of Variation (% CV);
$T_{max}$ values are given as median (min-max).

Results: The extent of abiraterone plasma exposures (dose-normalized to $AUC_{last}$) was increased to 7.1 fold higher in presence of food compared to fasted state following a single oral administration of Zytiga® in male Beagle dogs. In fed condition, relative bioavailability was 0.98 fold high for Example 7 compared to the fasted condition in dogs, which indicates plasma exposures were similar in fasted and fed condition with no food effect. There was no food effect observed in abiraterone acetate granules (example 7) following oral administration to male Beagle dogs.

We claim:

1. A pharmaceutical composition, comprising solid dispersion of amorphous abiraterone acetate, wherein said solid dispersion comprises:
   (a) from 2% to 50% by weight abiraterone acetate;
   (b) from 10% to 75% by weight one or more polymers;
   (c) from 10% to 70% by weight one or more surfactants;
   (d) from 5% to 50% by weight one or more plasticizers;
   (e) from 0.5% to 5% by weight at least one pH modifier;
   (f) from 2% to 10% by weight at least one disintegrating agent; and
   (g) from 0.01% to 1% by weight one or more preservatives.

2. The pharmaceutical composition according to claim 1, wherein one or more polymers selected from hydroxypropylmethylcellulose, poly (methacrylic acid-co-ethyl acrylate) 1:1, polyvinylpyrrolidone, hydroxypropyl cellulose, hydroxypropyl methylcellulose acetate succinate, pullulan, processed starch, and polyethylene oxide.

3. The pharmaceutical composition according to claim 1, wherein one or more surfactants selected from polysorbate 80, d-α-tocopheryl polyethylene glycol, propylene glycol monocaprylate, caprylocaproyl macrogol-8 glycerides, glycerylmonocaprylate, poloxamer 188, PEG-40 hydrogenated castor oil, and lecithin.

4. The pharmaceutical composition according to claim 1, wherein one or more plasticizers selected from polyethylene glycol 8000, polyethylene glycol 400, propylene glycol and glycerin triacetate.

5. The pharmaceutical composition according to claim 1, wherein pH modifier is selected from citric acid and ascorbic acid.

6. The pharmaceutical composition according to claim 1, wherein disintegrating agent is selected from crospovidone, croscarmellose sodium and sodium starch glycolate.

7. The pharmaceutical composition according to claim 1, wherein one or more preservatives selected from butylatedhydroxytoluene, butylatedhydroxyanisole, propyl gallate, and ethylenediaminetetraacetic acid.

8. The pharmaceutical composition according to claim 1, further comprises one or more pharmaceutically acceptable excipients selected from diluents, glidant, lubricants, sweetening agents, flavoring agents, coloring agents, effervescence agents, and a mixture thereof.

9. The pharmaceutical composition according to claim 8, wherein one or more pharmaceutically acceptable excipients selected from neotame, orange flavor, sunset yellow, sodium bicarbonate, citric acid, colloidal silicon dioxide, dibasic calcium phosphate anhydrous, crospovidone, magnesium stearate, sodium stearylfumarate, microcrystalline cellulose and a mixture thereof.

10. A pharmaceutical composition comprising solid dispersion, wherein said solid dispersion comprises based on the total weight of the composition:
    (a) from 2% to 5% by weight amorphous abiraterone acetate;
    (b) from 20% to 25% by weight hydroxypropylmethylcellulose;
    (c) from 20% to 25% by weight polysorbate 80;
    (d) from 0.5% to 2% by weight D-α-tocopheryl polyethylene glycol;
    (e) from 10% to 15% by weight propylene glycol monocaprylate;
    (f) from 1% to 5% by weight caprylocaproyl macrogol-8 glycerides;
    (g) from 15% to 25% by weight polyethylene glycol 8000;
    (h) from 5% to 10% by weight polyethylene glycol 400;
    (i) from 1% to 3% by weight poly (methacylic acid-co-ethyl acrylate) 1:1;
    (j) from 1% to 2% by weight citric acid;
    (k) from 3% to 5% by weight croscarmellose sodium; and
    (l) from 0.1% to 0.2% by weight butylatedhydroxytoluene;
    and optionally comprises one or more excipients selected from sweetening agents, flavoring agents, and coloring agents.

11. A pharmaceutical composition comprising solid dispersion, wherein said solid dispersion comprises based on the total weight of the composition:
    (a) from 2% to 5% by weight amorphous abiraterone acetate;
    (b) from 20% to 25% by weight hydroxypropylmethylcellulose;
    (c) from 20% to 25% by weight polysorbate 80;
    (d) from 0.5% to 2% by weight D-α-tocopheryl polyethylene glycol;
    (e) from 10% to 15% by weight propylene glycol monocaprylate;
    (f) from 1% to 5% by weight caprylocaproyl macrogol-8 glycerides;
    (g) from 15% to 25% by weight polyvinylpyrrolidone;
    (h) from 5% to 10% by weight polyethylene glycol 400;
    (i) from 1% to 3% by weight poly (methacrylic acid-co-ethyl acrylate) 1:1;
    (j) from 1% to 2% by weight citric acid;
    (k) from 3% to 5% by weight croscarmellose sodium; and
    (l) from 0.1% to 0.2% by weight butylatedhydroxytoluene.

12. The pharmaceutical composition according to claim 1, wherein the composition is an oral dosage form, selected from powders, granules, powders for reconstitution, granules for reconstitution, tablets, and capsules.

13. The pharmaceutical composition according to claim 12, wherein said oral dosage form comprises from 50 mg to 500 mg of amorphous abiraterone acetate in the form of solid dispersion.

14. The pharmaceutical composition according to claim 12, wherein said oral dosage form comprises 50 mg to 300 mg, 100 mg to 300 mg, or 200 mg to 300 mg of amorphous abiraterone acetate in the form of solid dispersion.

15. The pharmaceutical composition according to claim 12, wherein said oral dosage form comprises 50 mg, 100 mg, 150 mg, 200 mg, 250 mg, or 300 mg of amorphous abiraterone acetate in the form of solid dispersion.

16. The pharmaceutical composition according to claim 1, wherein the amorphous abiraterone acetate containing less than 30% crystalline abiraterone acetate.

17. The pharmaceutical composition according to claim 1, wherein the amorphous abiraterone acetate containing less than 10% crystalline abiraterone acetate.

18. The pharmaceutical composition according to claim 1, for use in the treatment of prostate cancer.

19. The pharmaceutical composition according to claim 18, wherein said prostate cancer is selected from metastatic castration-resistant prostate cancer, non- metastatic castration-resistant prostate cancer, metastatic castration-sensitive prostate cancer, or non-metastatic castration-sensitive prostate cancer.

20. A method for the preparation of the pharmaceutical composition of claim 1, comprising the step of:
  a) dissolving abiraterone acetate and pharmaceutically acceptable excipients in a solvent mixture to form a homogenous solution;
  b) drying the homogenous solution of step (a) at a controlled temperature to get solid dispersion containing amorphous abiraterone acetate;
  c) milling the solid dispersion obtained in step (b) to obtain granules;
  d) optionally mixing and blending the granules obtained in step (c) and one or more pharmaceutically acceptable excipients;
  e) processing the blend obtained in step (d) into pharmaceutical dosage forms, wherein said drying comprises pouring homogeneous solution as a thin sheet and drying for 3 hr at a temperature less than 40° C. or less than 50° C., wherein the thickness of the said thin sheet is less than 1500 μm.

\* \* \* \* \*